United States Patent
Chapman et al.

(10) Patent No.: US 11,305,283 B2
(45) Date of Patent: Apr. 19, 2022

(54) MICRO-FLUIDIC DEVICES FOR ASSAYING BIOLOGICAL ACTIVITY

(71) Applicant: Berkeley Lights, Inc., Emeryville, CA (US)

(72) Inventors: Kevin T. Chapman, Santa Monica, CA (US); Daniele Malleo, El Cerrito, CA (US); J. Tanner Nevill, El Cerrito, CA (US); Steven W. Short, Pleasanton, CA (US); Mark P. White, San Francisco, CA (US); M. Jimena Loureiro, Albany, CA (US)

(73) Assignee: Berkeley Lights, Inc., Emeryville, CA (US)

( * ) Notice: Subject to any disclaimer, the term of this patent is extended or adjusted under 35 U.S.C. 154(b) by 433 days.

(21) Appl. No.: 16/509,166

(22) Filed: Jul. 11, 2019

(65) Prior Publication Data

US 2020/0078788 A1    Mar. 12, 2020

Related U.S. Application Data

(63) Continuation of application No. 15/843,122, filed on Dec. 15, 2017, now Pat. No. 10,376,886, which is a (Continued)

(51) Int. Cl.
*B01L 3/00*    (2006.01)
*G01N 33/68*    (2006.01)
(Continued)

(52) U.S. Cl.
CPC ........ *B01L 3/502761* (2013.01); *B03C 5/005* (2013.01); *B03C 5/026* (2013.01);
(Continued)

(58) Field of Classification Search
CPC ..... B01L 2200/0647; B01L 2200/0668; B01L 2300/0636; B01L 2300/0816;
(Continued)

(56) References Cited

U.S. PATENT DOCUMENTS 6,294,063 B1    9/2001 Becker et al.
6,541,213 B1    4/2003 Weigl et al.
(Continued)

FOREIGN PATENT DOCUMENTS

CN    101548004 A    9/2009
CN    101580797 A    11/2009
(Continued)

OTHER PUBLICATIONS

Bocchi et al. "Inverted open microwells for cell trapping, cell aggregate formation and parallel recovery of live cells" Lab on a Chip, 2012, 12, 3168-3176.
(Continued)

*Primary Examiner* — Jennifer Wecker
(74) *Attorney, Agent, or Firm* — Kenneth E. Horton; Barnes & Thornburg LLP

(57) ABSTRACT

Biological activity in holding pens in a micro-fluidic device can be assayed by placing in the holding pens capture objects that bind a particular material of interest produced by the biological activity. The biological material of interest that binds to each capture object can then be assessed, either in the micro-fluidic device or after exporting the capture object from the micro-fluidic device. The assessment can be utilized to characterize the biological activity in each holding pen. The biological activity can be production of the biological material of interest. Thus, the biological activity can correspond to or arise from one or more biological cells. Biological cells within a holding pen can be clonal cell colonies. The biological activity of each clonal cell colony
(Continued)

can be assayed while maintaining the clonal status of each colony.

20 Claims, 17 Drawing Sheets

Related U.S. Application Data continuation of application No. 14/521,447, filed on Oct. 22, 2014, now Pat. No. 9,889,445, which is a continuation-in-part of application No. 14/520,510, filed on Oct. 22, 2014, now Pat. No. 9,617,145.

(60) Provisional application No. 62/058,658, filed on Oct. 1, 2014, provisional application No. 61/996,962, filed on Oct. 22, 2013, provisional application No. 61/996,973, filed on Oct. 22, 2013, provisional application No. 61/996,969, filed on Oct. 22, 2013.

(51) Int. Cl.
*G01N 33/50* (2006.01)
*G01N 33/543* (2006.01)
*G01N 15/14* (2006.01)
*B03C 5/00* (2006.01)
*B03C 5/02* (2006.01)

(52) U.S. Cl.
CPC ....... *G01N 15/1484* (2013.01); *G01N 33/505* (2013.01); *G01N 33/5023* (2013.01); *G01N 33/5047* (2013.01); *G01N 33/5052* (2013.01); *G01N 33/54313* (2013.01); *G01N 33/6854* (2013.01); *B01L 2200/0647* (2013.01); *B01L 2200/0668* (2013.01); *B01L 2300/0636* (2013.01); *B01L 2300/087* (2013.01); *B01L 2300/0816* (2013.01); *B01L 2300/0864* (2013.01); *B01L 2400/0454* (2013.01); *B03C 2201/26* (2013.01)

(58) Field of Classification Search
CPC ....... B01L 2300/0864; B01L 2300/087; B01L 2400/0454; B01L 3/502761; B03C 2201/26; B03C 5/005; B03C 5/026; G01N 15/1484; G01N 33/5023; G01N 33/5047; G01N 33/505; G01N 33/5052; G01N 33/54313; G01N 33/6854
See application file for complete search history.

(56) References Cited

U.S. PATENT DOCUMENTS

| | | | |
|---|---|---|---|
| 6,942,776 B2 | 9/2005 | Medoro | |
| 6,958,132 B2 | 10/2005 | Chiou et al. | |
| 7,090,759 B1 | 8/2006 | Seul | |
| 7,612,355 B2 | 11/2009 | Wu et al. | |
| 7,956,339 B2 | 6/2011 | Ohta et al. | |
| 2003/0008364 A1 | 1/2003 | Wang et al. | |
| 2003/0224528 A1 | 12/2003 | Chiou et al. | |
| 2004/0072278 A1 | 4/2004 | Chou et al. | |
| 2004/0191789 A1 | 9/2004 | Manaresi et al. | |
| 2004/0197905 A1 | 10/2004 | Hafeman | |
| 2005/0112548 A1 | 5/2005 | Segawa et al. | |
| 2005/0129581 A1 | 6/2005 | McBride et al. | |
| 2005/0175981 A1 | 8/2005 | Voldman et al. | |
| 2005/0226781 A1 | 10/2005 | Yun et al. | |
| 2006/0091015 A1 | 5/2006 | Lau | |
| 2006/0154361 A1 | 7/2006 | Wikswo et al. | |
| 2007/0095669 A1 | 5/2007 | Lau et al. | |
| 2007/0183934 A1 | 8/2007 | Diercks et al. | |
| 2007/0240495 A1 | 10/2007 | Hirahara | |
| 2007/0242105 A1 | 10/2007 | Srinivasan et al. | |
| 2008/0085556 A1 | 4/2008 | Graefing et al. | |
| 2008/0274493 A1 | 11/2008 | Quake et al. | |
| 2008/0302732 A1 | 12/2008 | Soh et al. | |
| 2008/0318203 A1 | 12/2008 | Tran et al. | |
| 2009/0023608 A1 | 1/2009 | Hung et al. | |
| 2009/0170186 A1 | 7/2009 | Wu et al. | |
| 2010/0003666 A1 | 1/2010 | Lee et al. | |
| 2010/0101960 A1 | 4/2010 | Ohta et al. | |
| 2010/0263599 A1 | 10/2010 | Yanik et al. | |
| 2011/0053151 A1 | 3/2011 | Hansen et al. | |
| 2011/0117634 A1* | 5/2011 | Halamish | C12M 23/16 435/283.1 |
| 2011/0262906 A1 | 10/2011 | Dimov et al. | |
| 2012/0009671 A1 | 1/2012 | Hansen et al. | |
| 2012/0015347 A1 | 1/2012 | Singhal et al. | |
| 2012/0015382 A1 | 1/2012 | Weitz et al. | |
| 2012/0024708 A1 | 2/2012 | Chiou et al. | |
| 2012/0118740 A1 | 5/2012 | Garcia et al. | |
| 2012/0156675 A1 | 6/2012 | Luerssen et al. | |
| 2012/0325665 A1 | 12/2012 | Chiou et al. | |
| 2013/0118905 A1 | 5/2013 | Morimoto et al. | |
| 2013/0130232 A1 | 5/2013 | Weibel et al. | |
| 2013/0171628 A1 | 7/2013 | Di Carlo et al. | |
| 2013/0190212 A1 | 7/2013 | Handique et al. | |
| 2013/0204076 A1 | 8/2013 | Han et al. | |
| 2013/0252258 A1* | 9/2013 | Bocchi | G01N 33/56972 435/7.21 |
| 2013/0261021 A1 | 10/2013 | Bocchi et al. | |
| 2014/0116881 A1* | 5/2014 | Chapman | G01N 27/44791 204/451 |
| 2014/0124370 A1 | 5/2014 | Short et al. | |
| 2015/0151298 A1 | 6/2015 | Hobbs et al. | |
| 2015/0151307 A1 | 6/2015 | Breinlinger et al. | |
| 2015/0167043 A1 | 6/2015 | Goluch et al. | |
| 2016/0252495 A1 | 9/2016 | Ricicova et al. | |

FOREIGN PATENT DOCUMENTS

| | | |
|---|---|---|
| CN | 201427971 | 3/2010 |
| CN | 102215966 A | 10/2011 |
| CN | 102296028 A | 12/2011 |
| CN | 102580794 A | 7/2012 |
| CN | 101580797 A | 11/2018 |
| EP | 1065378 A2 | 1/2001 |
| EP | 2052784 A1 | 4/2009 |
| JP | 2004528156 A | 9/2004 |
| JP | 2005292115 A | 10/2005 |
| JP | 2008136475 A | 6/2008 |
| JP | 2010060567 A | 3/2010 |
| JP | 2012522518 A | 9/2012 |
| WO | 2002044689 A2 | 6/2002 |
| WO | 2004089810 A2 | 10/2004 |
| WO | 2006058645 A1 | 6/2006 |
| WO | 2007008609 A3 | 4/2009 |
| WO | 2007024701 A3 | 5/2009 |
| WO | 2009130694 A2 | 10/2009 |
| WO | 2009146143 A2 | 12/2009 |
| WO | 2010005593 A1 | 1/2010 |
| WO | 2010147078 A1 | 12/2010 |
| WO | 2011160430 A1 | 12/2011 |
| WO | 2012037030 A2 | 3/2012 |
| WO | 2012050981 A1 | 4/2012 |
| WO | 2012058637 A2 | 5/2012 |
| WO | 2014070873 A1 | 5/2014 |
| WO | 2015061497 A1 | 4/2015 |
| WO | 2015061462 A1 | 7/2015 |

OTHER PUBLICATIONS

Abstract, "Recent Applications of Microfluidic Technology in the Field of Cell Biology" Chinese Journal of Cell Biology, 2011, 33(11): 1254-1266.
Yao L, Bai L, Wu L Q, et al. "Recent applications of microfluidic technology in the field of cell biology" Chinese Journal of Cell Biology, 2011, 33: 1254-1266 Machine Translation.
Chen et al., Microfluidic approaches for cancer cell detection, characterization, and separation, Lab on a Chip 12:1753 (2012).

(56) References Cited

OTHER PUBLICATIONS

Chiou et al., "Massively parallel manipulation of single cells and microparticles using optical images," Nature, vol. 436 (Jul. 21, 2005), pp. 370-372.
Chung et al., Imaging Single-Cell Signaling Dynamics with a Deterministic High-Density Single-Cell Trap Array, Anal. Chem. 83(18):7044-7052 (2011).
Dicarlo et al., "Dynamic Single Cell Analysis for Quantitative Biology," Analytical Chemistry (Dec. 1, 2006), pp. 7918-7925.
Dishinger et al., "Serial Immunoassays in Parallel on a Microfluidic Chip for Monitoring Hormone Secretion from Living Cells," Analytical Chemistry vol. 79, No. 3 (Feb. 1, 2007), pp. 947-954.
Fuchs et al., "Electronic sorting and recovery of single live cells from microlitre sized samples" Lab on a Chip 6:121-26 (2006).
Gascoyne, Peter et al., "Dielectrophoretic Separation of Cancer Cells from Blood", IEEE Trans Ind Appl. 1997, vol. 33(3), pp. 67-678, Dec. 2009.
Han et al., Integration of single oocyte trapping, in vitro fertilization and embryo culture in a microwell-structured microfluidic device, Lab on a Chip 10:2848-54 (2010).
Hsu, HY et al., "Sorting of Differentiated Neurons Using Phototransistor-Based Optoelectronic Tweezers for Cell Replacement Therapy of Neurodegenerative Diseases", Transducers 2009, Denver, CO USA Jun. 2009, download dated Nov. 23, 2009 from IEEE Xplore, 4 pages.
Hung et al., Continuous Perfusion Microfluidic Cell Culture Array for High-Throughput Cell-Based Assays, Biotech and Bioengineering 89(1): 1-8 (2004). Dec. 3, 2004.
Hur et al., High-Throughput Size Based Rare Cell Isolation Using Microscale Vortices, Intl Conf on Miniaturized Systems (2010).
Hur et al., High-throughput Size-Based Rare Cell Enrichment Using Microscale Vortices, Biomicrofluidics 5:022206 (2011).
Iliescu et al., Continuous Field-Flow Separation of Particle Populations in a Dielectrophoretic Chip with Three Dimensional Electrodes, Applied Physics Letters 90:234104 (2007).
Nevill et al., Integrated microfluidic cell culture and lysis on a chip, Lab on a Chip 7:1689-95 (2007).
Somaweera H. et al., Generation of a Chemical Gradient Across an Array of 256 Cell Cultures in a Single Chip. Analyst, Oct. 7, 2013, vol. 138, No. 19, pp. 5566-5571.
Valley et al., "A unified platform for optoelectrowetting and optoelectronic tweezers", Lab on a Chip 11:1292-97, Feb. 22, 2011.
Valley et al., Optoelectronic Tweezers as a Tool for Parallel Single-Cell Manipulation and Simulation, IEEE Transactions on Biomedical Circuits and Systems, vol. 3, No. 6 (Dec. 2009), pp. 424-431.
Yi et al., "Microfluidics technology for manipulation and analysis of biological cells," Analytica Chimica Acta 560 (2006), pp. 1-23.
Young et al., Fundamentals of microfluidic cell culture in controlled microenvironments, Chem Soc Rev 39(3): 1036-48 (2010).
Z REPORT_International Search Report and Written Opinion for PCT Application Serial No. PCT/2014/061787 (dated Feb. 25, 2015), 11 pages.
Z REPORT_International Search Report and Written Opinion for PCT Application Serial No. PCT/2014/061848 (dated Jan. 22, 2015), 15 pages.

\* cited by examiner

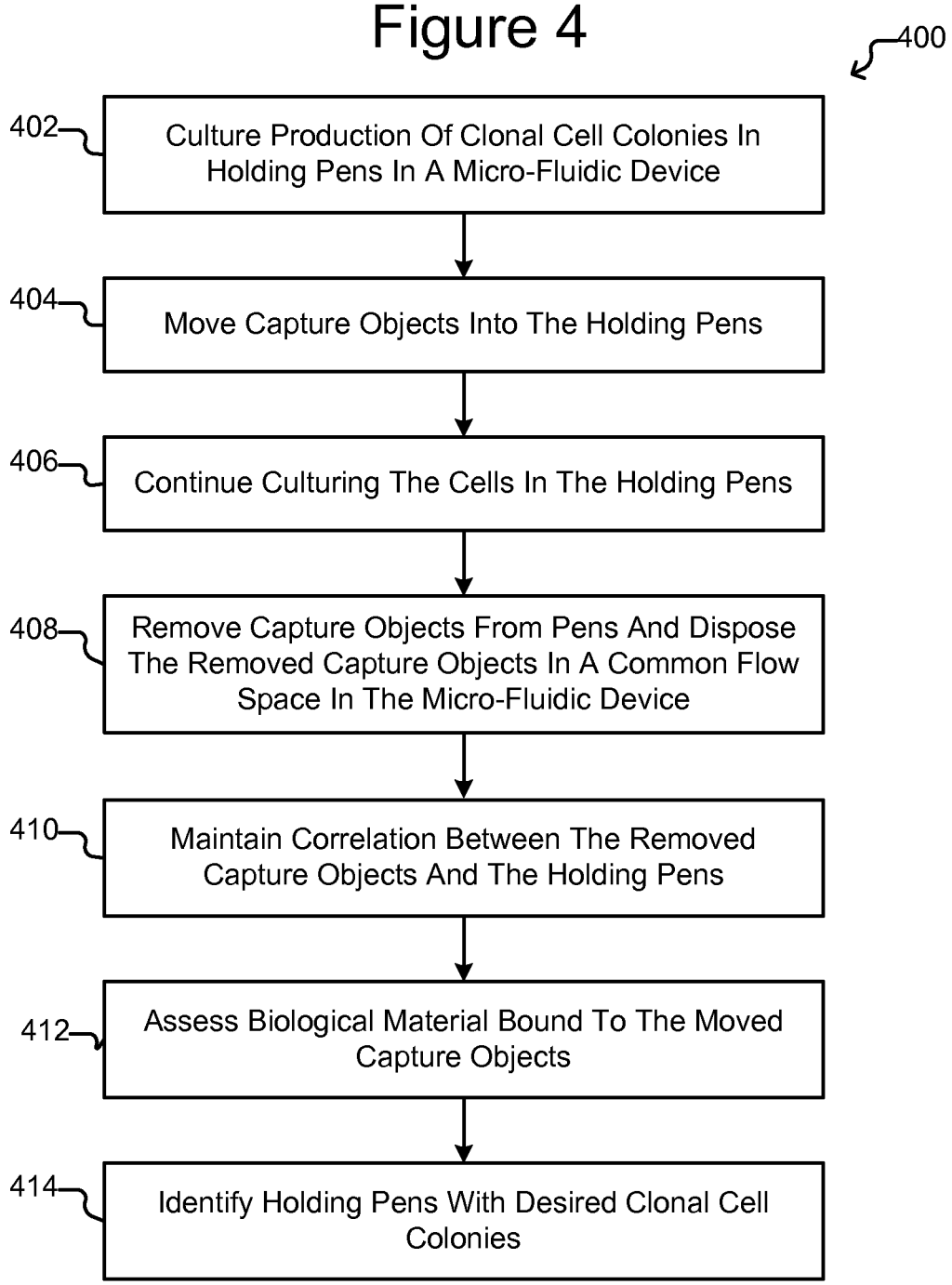

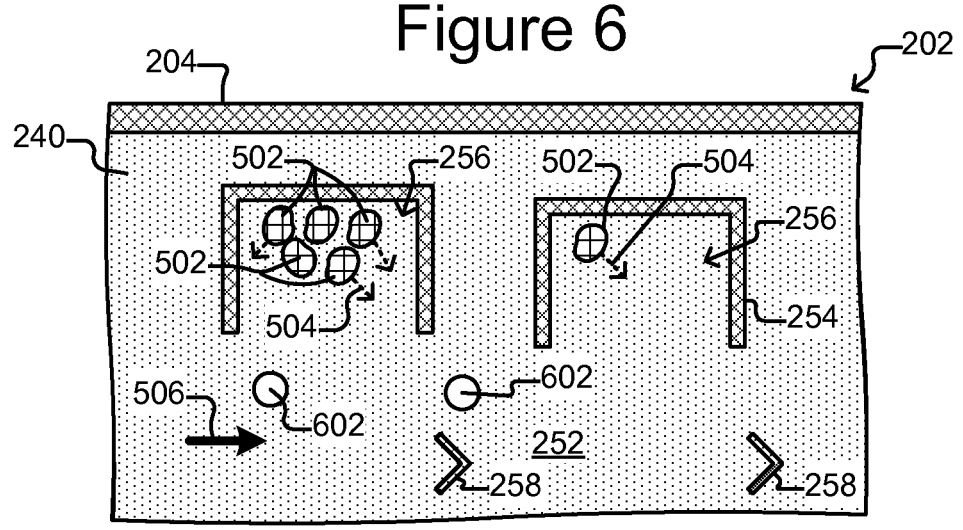
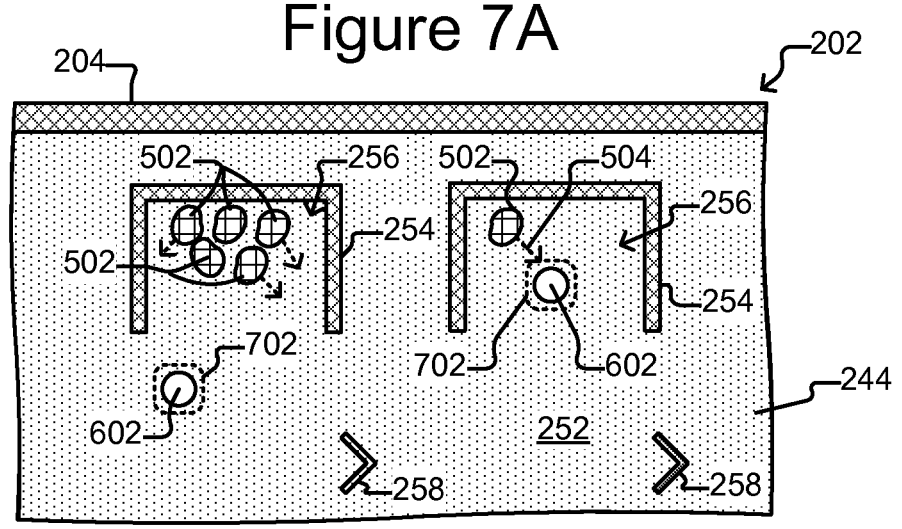

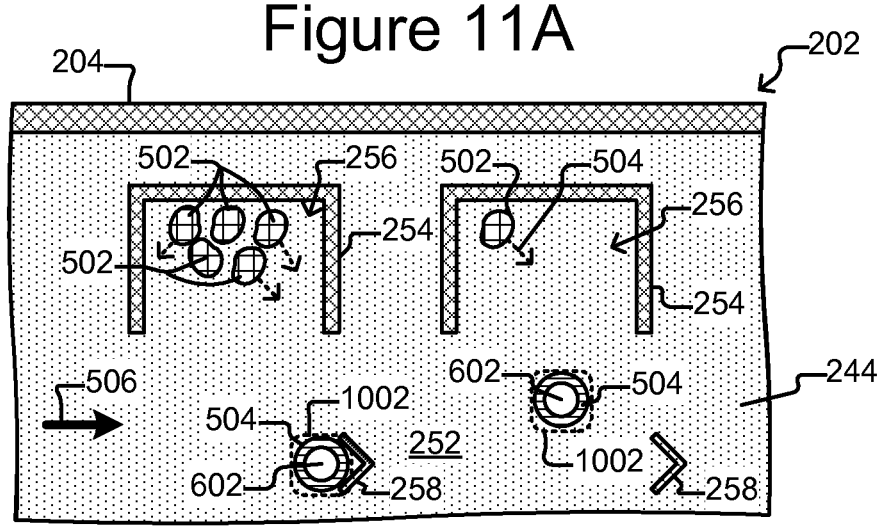
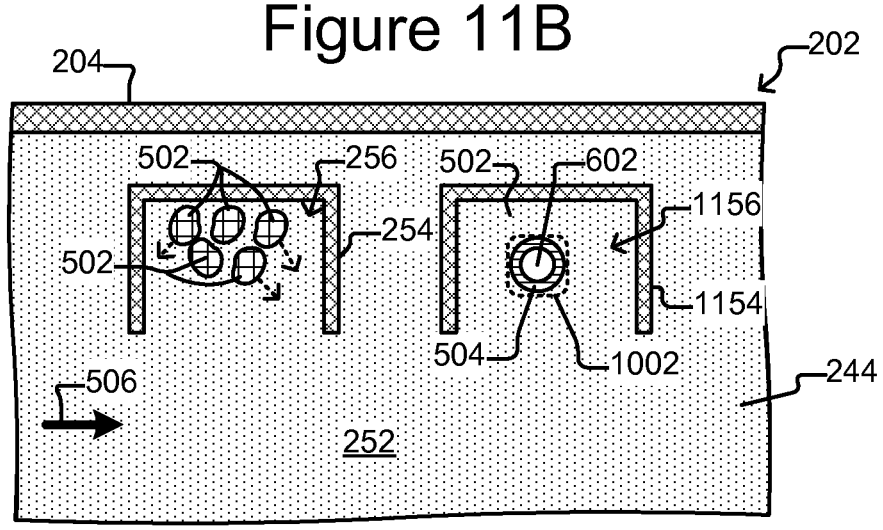

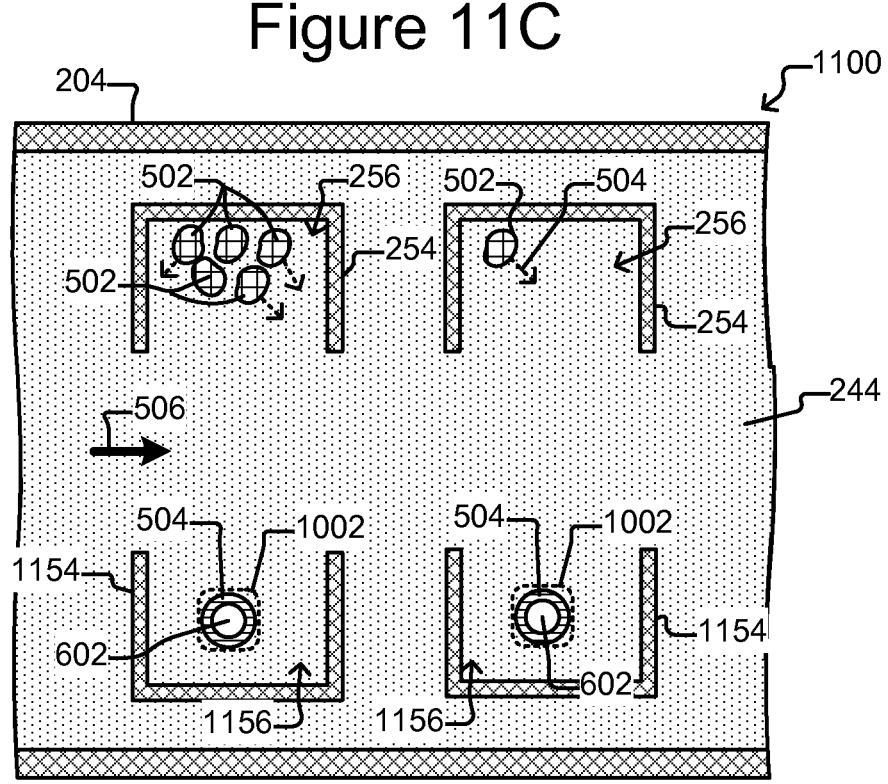
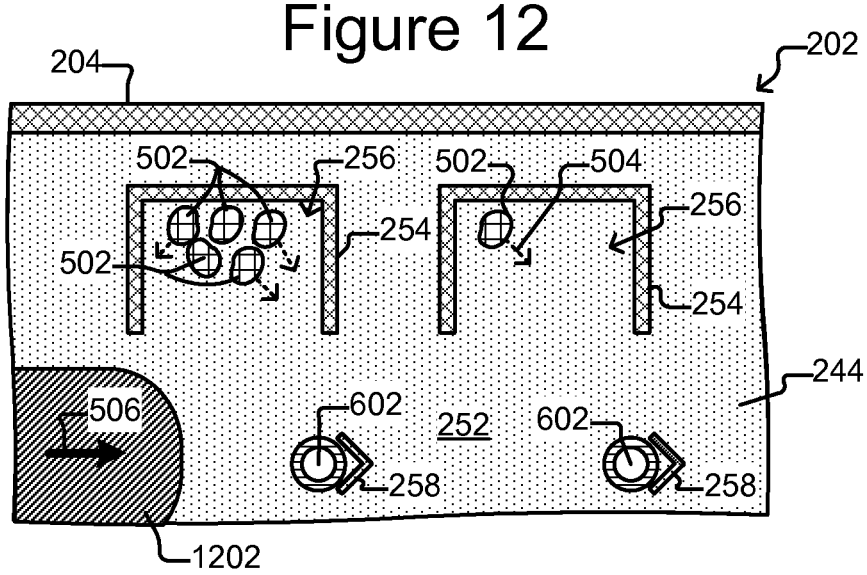

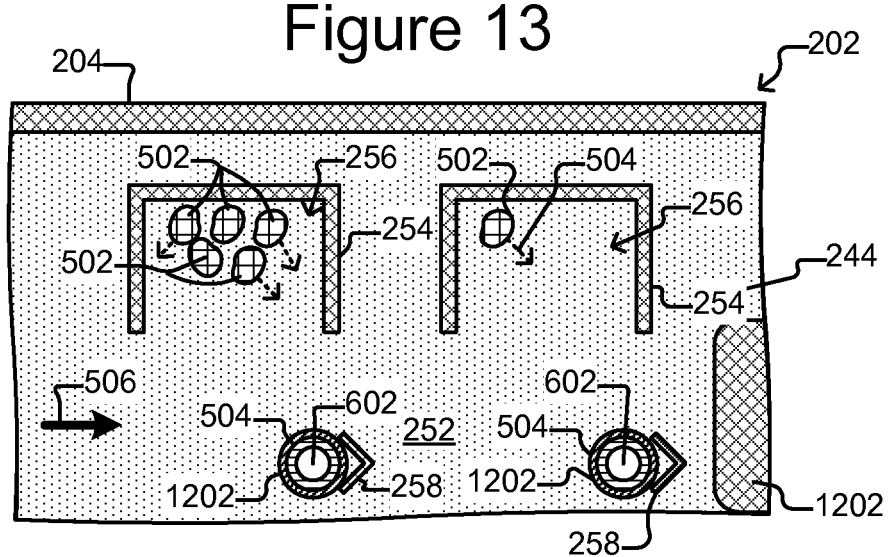
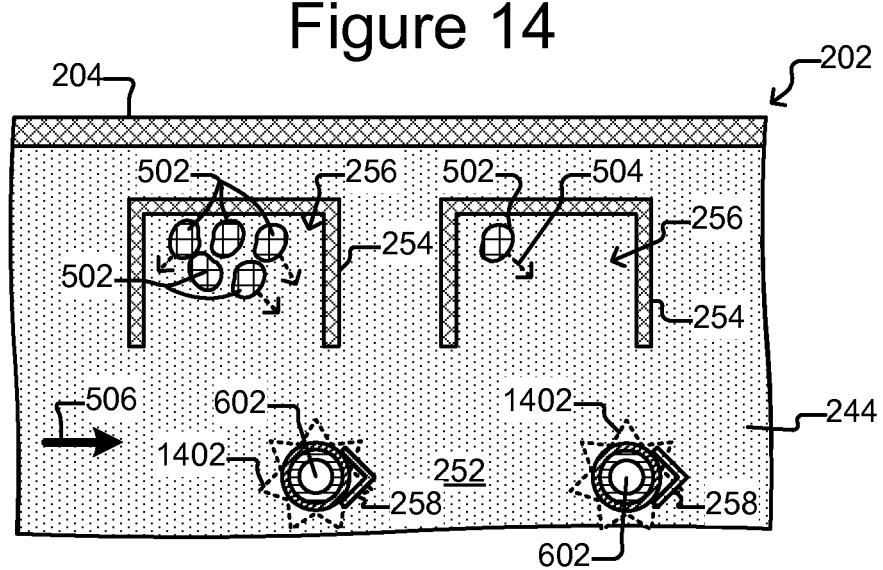

MICRO-FLUIDIC DEVICES FOR ASSAYING BIOLOGICAL ACTIVITY

CROSS REFERENCE TO RELATED APPLICATION(S)

This application is a continuation application of U.S. application Ser. No. 15/843,122, which is a continuation application of U.S. application Ser. No. 14/521,447, which claims the benefit under 35 U.S.C. § 119(e) of U.S. Provisional Patent Application No. 61/996,973, filed on Oct. 22, 2013; U.S. Provisional Patent Application No. 61/996,962, filed on Oct. 22, 2013; U.S. Provisional Patent Application No. 61/996,969, filed on Oct. 22, 2013; and U.S. Provisional Patent Application No. 62/058,658, filed on Oct. 1, 2014. U.S. application Ser. No. 14/521,447 is also a continuation-in-part under 35 U.S.C. § 120 of U.S. patent application Ser. No. 14/520,150, filed on Oct. 22, 2014. Each of the above disclosures is herein incorporated by reference in its entirety.

BACKGROUND

In biosciences and related fields, it can be useful to assay biological activity of micro-objects such as cells. Some embodiments of the present invention include apparatuses and processes for assaying biological activity in holding pens of a micro-fluidic device.

SUMMARY

In some embodiments, the invention provides processes for assaying biological activity in a micro-fluidic device. The biological activity can be the production of a biological material of interest, such as by a biological cell. Thus, the process can include culturing one or more biological cells that produce a biological material of interest in a holding pen of a micro-fluidic device. The process can further include introducing one or more capture micro-objects into the holding pen and allowing the biological material of interest produced by the one or more biological cells to bind to the one or more capture micro-objects. The capture micro-objects can include, for example, a binding substance that specifically binds said biological material of interest. The process can also include assessing the capture micro-objects for bound biological material of interest.

In certain embodiments, the one or more capture micro-objects are removed from the holding pen after allowing the biological material of interest to bind to the one or more capture micro-objects but before assessing the capture micro-objects for bound biological material of interest. Removing the one or more capture micro-objects can include moving the one or more capture micro-objects to an assay region located within the micro-fluidic device. In certain embodiments, the assay region is a stop located within a channel in the micro-fluidic device, a chamber located within the micro-fluidic device, or the like. Regardless, the assay region can be located adjacent to the holding pen from with the one or more capture micro-objects are removed. Alternatively, or in addition, removing the one or more capture micro-objects can include moving the one or more capture micro-objects to a channel in said micro-fluidic device and then exporting the one or more capture micro-objects from said micro-fluidic device.

In certain embodiments, removing the one or more capture micro-objects includes creating a light trap that traps at least one of the capture micro-objects while it is in the holding pen. The light trap can include a light pattern, projected onto an inner surface of the micro-fluidic device, that surrounds the at least one capture micro-object and activates electrodes, such as dielectrophoresis (DEP) electrodes, within the micro-fluidic device. Moving the light trap from the holding pen to the channel and/or assay region of the micro-fluidic device can cause the trapped capture micro-objects to move accordingly.

In certain embodiments, the one or more capture micro-objects are magnetic. In related embodiments, removing the one or more capture micro-objects can involve applying a magnetic field to the micro-fluidic device.

In certain embodiments, capture micro-objects that have been removed from the holding pen can remain associated with the holding pen. For example, a correlation can be maintained between the capture micro-objects and the holding pen from which they have been removed. In this manner, when a micro-fluidic device contains a plurality of holding pens, data obtained from capture micro-objects that have been removed from their holding pen can be tracked back to the appropriate holding pen.

In certain embodiments, assessing the capture micro-objects for bound biological material of interest is performed while the capture micro-objects are in the holding pen.

In certain embodiments, assessing capture micro-objects for bound biological material of interest can involve determining the type of biological material of interest bound to the capture micro-objects. In certain embodiments, assessing capture micro-objects for bound biological material of interest can involve determining an activity of the biological material of interest bound to the capture micro-objects. In certain embodiments, assessing capture micro-objects for bound biological material of interest can involve determining the amount of said biological material of interest bound to the capture micro-objects. Any such determination can include mixing (and/or binding) assay material with biological material of interest bound to the capture micro-objects and detecting an association between the capture micro-objects and the assay material. For example, if the assay material is capable of producing detectable radiation, the determination can involve detecting an association between the capture micro-objects and radiation originating from the assay material. The determination can further involve washing unbound and/or unreacted assay material away from the capture micro-objects before detecting an association between the micro-objects and radiation originating from the assay material. Alternatively, or in addition, the determination can further involve determining whether radiation associated with the capture micro-objects corresponds to a predetermined characteristic. For example, the radiation may have a characteristic wavelength.

In certain embodiments, the biological material of interest is a protein, such as a therapeutic protein, an antibody, a growth factor, a cytokine, a cancer antigen, an infectious antigen associated with a virus or other pathogen, a secreted protein, or any other protein produced and/or released by a biological cell. In certain embodiments, the biological material of interest is a protein, a nucleic acid, a carbohydrate, a lipid, a hormone, a metabolite, a small molecule, a polymer, or any combination thereof. In certain embodiments, the binding substance of the capture micro-objects has a binding affinity of at least 1 µM, 100 nM, 50 nM, 25 nM, 10 nM, 5 nM, 1 nM or stronger for the biological material of interest.

In certain embodiments, there is a single biological cells in the holding pen. In other embodiments, there are two or more biological cells in the holding pen. In certain embodiments, the biological cells in the holding pen are a clonal colony. In certain embodiments, a single capture micro-object is introduced into the holding pen. In other embodiments, two or more (e.g., a plurality of) capture micro-object are introduced into the holding pen. In these latter embodiments, each capture micro-object of the plurality can have a binding substance that differs from the binding substance of the other capture micro-objects in the plurality.

In certain embodiments, the biological material of interest is an antibody, such as a candidate therapeutic antibody. In related embodiments, the processes can include a plurality of capture micro-objects, each of which has a binding substance which binds to a different antibody isotype. In other related embodiments, the processes can include a plurality of capture micro-objects, each of which has a binding substance corresponding to a different epitope of the antigen recognized by the antibody. In still other related embodiments, the processes can include a plurality of capture micro-objects, one of which has a binding substance corresponding to an antigen recognized by said antibody or an epitope thereof. The remaining capture micro-objects in the plurality can have a binding substance corresponding to a homolog of the antigen or an epitope thereof. The homologous antigen or epitope thereof can be from a different species.

In some embodiments, the invention provides processes for assaying the production of n different biological materials of interest in a micro-fluidic device. The processes can include culturing one or more biological cells in a holding pen of a micro-fluidic device, wherein the one or more cells produce n different biological materials of interest. The processes can further include introducing n different types of capture micro-objects into the holding pen, each type having a binding substance that specifically binds to one of said n different biological materials of interest, and allowing the n different biological materials of interest produced by the biological cells to bind to the n different types of capture micro-objects. The processes can also include assessing the n different types of capture micro-objects for bound biological materials of interest. In certain embodiments, the result of such assessment is positive if at least one of the n different biological materials of interest specifically binds to one of the n different types of capture micro-objects. In other embodiments, the result of such assessment is positive if at least two of the n different biological materials of interest each specifically binds to one of the n different types of capture micro-objects. In still other embodiments, the result of such assessment is positive if all n different biological materials of interest each specifically binds to one of the n different types of capture micro-objects.

In certain embodiments, the n different types of capture micro-objects are introduced into the holding pen simultaneously. In other embodiments, the n different types of capture micro-objects are introduced into the holding pen sequentially.

In some embodiments, the processes for assaying the production of n different biological materials of interest in a micro-fluidic device include introducing one or more y-material capture micro-objects into the holding pen, each y-material capture micro-object having y different binding substances, each of which specifically binds to one of the n different biological materials of interest produced by the one or more biological cells. The processes can further include allowing the n different biological materials of interest produced by the one or more biological cells to bind to said y-material capture micro-objects. In addition, the processes can include assessing the y-material capture micro-objects for bound biological materials of interest.

For any of the foregoing processes, the micro-fluidic device can include a plurality of holding pens, each of which contains one or more biological cells, which can be assayed sequentially or in parallel.

In some embodiments, the invention provides a micro-fluidic device. The micro-fluidic device can include an enclosure having a channel, a holding pen, and an assay region. The holding pen can include an isolation region and a connection region, with the connection region having a proximal opening to the channel and a distal opening to the isolation region. The assay region can be located adjacent to the holding pen. For example, the assay region can include a stop located within the channel. The stop can be located directly across the channel from or just outside the proximal opening of the connection region. Alternatively, the assay region can include an assay chamber. The assay chamber can be located beside the holding pen or directly across the channel from the proximal opening of the connection region of the holding pen. In some embodiments, the assay chamber substantially lacks an isolation region (e.g., less than 50% of the volume of the assay chamber can be isolated from the bulk flow of medium that is flowing through the channel). In certain embodiments, the micro-fluidic device can also include a means for generating a magnetic force within the enclosure. Such means can be, for example, a magnet.

BRIEF DESCRIPTION OF THE DRAWINGS

FIG. 4 is an example of a process in which biological activity of cells in holding pens can be assayed according to some embodiments of the invention.

FIG. 6 illustrates an example of the moving step of FIG. 4 according to some embodiments of the invention.

FIG. 7A illustrates another example of the moving step of FIG. 4 according to some embodiments of the invention.

FIG. 11A illustrates another example of the removing step of FIG. 4 according to some embodiments of the invention.

FIG. 11B illustrates a variation of the removing step of FIG. 4 in which the capture object is removed from a holding pen that contains biological cells and placed into an assay pen.

FIG. 11C illustrates another variation of the removing step of FIG. 4 in which the capture object is removed from a holding pen that contains biological cells and placed into an assay pen.

FIGS. 12 through 14 show an example of the assessing step of FIG. 4 according to some embodiments of the invention.

DETAILED DESCRIPTION OF EXEMPLARY EMBODIMENTS

Figure 1:
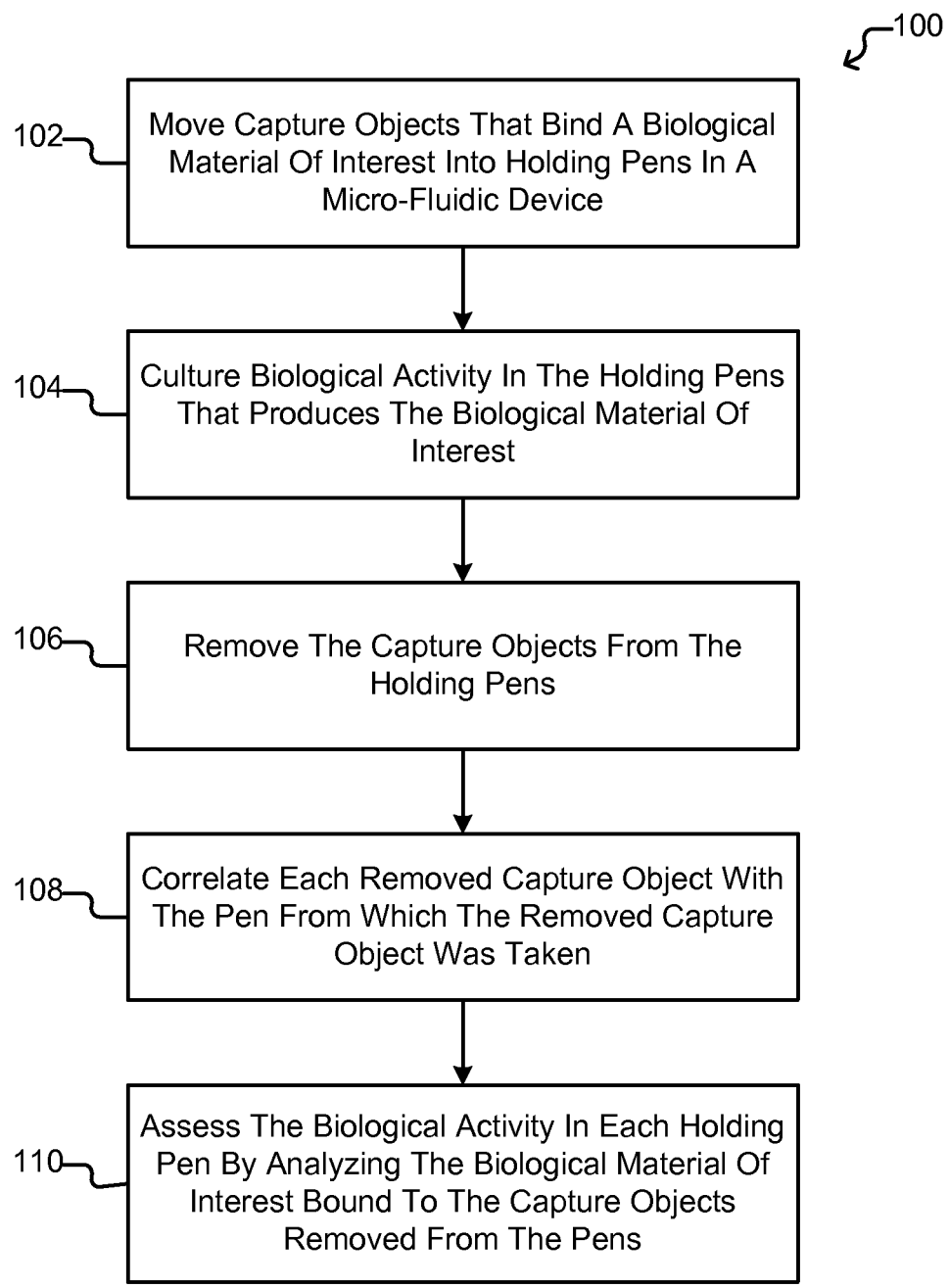
FIG. 1 is an example of a process for assaying biological activity in holding pens of a micro-fluidic device according to some embodiments of the invention.

This specification describes exemplary embodiments and applications of the invention. The invention, however, is not limited to these exemplary embodiments and applications or to the manner in which the exemplary embodiments and applications operate or are described herein. Moreover, the Figures may show simplified or partial views, and the dimensions of elements in the Figures may be exaggerated or otherwise not in proportion for clarity. In addition, as the terms "on," "attached to," or "coupled to" are used herein, one element (e.g., a material, a layer, a substrate, etc.) can be "on," "attached to," or "coupled to" another element regardless of whether the one element is directly on, attached, or coupled to the other element or there are one or more intervening elements between the one element and the other element. Also, directions (e.g., above, below, top, bottom, side, up, down, under, over, upper, lower, horizontal, vertical, "x," "y," "z," etc.), if provided, are relative and provided solely by way of example and for ease of illustration and discussion and not by way of limitation. In addition, where reference is made to a list of elements (e.g., elements a, b, c), such reference is intended to include any one of the listed elements by itself, any combination of less than all of the listed elements, and/or a combination of all of the listed elements.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, the term "substantially" means within ten percent. The term "ones" means more than one.

As used herein, the terms "capture object" and "capture micro-object" are used interchangeably and can encompass one or more of the following: inanimate micro-objects such as microparticles, microbeads (e.g., polystyrene beads, Luminex™ beads, or the like), magnetic beads, microrods, microwires, quantum dots, and the like; biological micro-objects such as cells (e.g., cells obtained from a tissue or fluid sample, blood cells, hydridomas, cultured cells, cells from a cell line, cancer cells, infected cells, transfected and/or transformed cells, reporter cells, and the like), liposomes (e.g, synthetic or derived from membrane preparations), lipid nanorafts, and the like; or a combination of inanimate micro-objects and biological micro-objects (e.g., microbeads attached to cells, liposome-coated micro-beads, liposome-coated magnetic beads, or the like). Lipid nanorafts have been described, e.g., in Ritchie et al. (2009) "Reconstitution of Membrane Proteins in Phospholipid Bilayer Nanodiscs," Methods Enzymol., 464:211-231.

As used herein, the terms "specific binding" and "specifically binds" refer to an interaction between a ligand and a receptor in which a specific surface of the ligand binds to a specific surface on the receptor such that ionic bonds, hydrogen bonds, and/or van der Waals forces hold the ligand and the receptor together in a specific conformation. The ligand can be a biological material of interest, such as a protein (e.g., a therapeutic protein, an antibody, a growth factor, a cytokine, a cancer antigen, an infectious antigen associated with a virus or other pathogen, a secreted protein, or any other protein produced and/or released by a biological cell), a nucleic acid, a carbohydrate, a lipid, a hormone, a metabolite, or any combination thereof. The receptor can be a binding substance, e.g., a biological or chemical molecule, such as a protein (e.g., a therapeutic protein, an antibody, a growth factor, a cytokine, a cancer antigen, an infectious antigen associated with a virus or other pathogen, a secreted protein, or any other protein produced and/or released by a biological cell), a nucleic acid, a carbohydrate, a lipid, a hormone, a metabolite, a small molecule, a polymer, or any combination thereof. Specific binding of a ligand to a receptor is associated with a quantifiable binding affinity. The binding affinity can be represented, for example, as a dissociation constant, Kd.

The term "flow," as used herein with reference to a liquid, refers to bulk movement of the liquid primarily due to any mechanism other than diffusion. For example, flow of a medium can involve movement of the fluidic medium from one point to another point due to a pressure differential between the points. Such flow can include a continuous, pulsed, periodic, random, intermittent, or reciprocating flow of the liquid, or any combination thereof. When one fluidic medium flows into another fluidic medium, turbulence and mixing of the media can result.

The phrase "substantially no flow" refers to a rate of flow of a liquid that is less than the rate of diffusion of components of a material (e.g., an analyte of interest) into or within the liquid. The rate of diffusion of components of such a material can depend on, for example, temperature, the size of the components, and the strength of interactions between the components and the fluidic medium.

As used herein in reference to a fluidic medium, "diffuse" and "diffusion" refer to thermodynamic movement of a component of the fluidic medium down a concentration gradient.

As used herein in reference to different regions within a microfluidic device, the phrase "fluidically connected" means that, when the different regions are substantially filled with fluid, such as fluidic media, the fluid in each of the regions is connected so as to form a single body of fluid. This does not mean that the fluids (or fluidic media) in the different regions are necessarily identical in composition. Rather, the fluids in different fluidically connected regions of a microfluidic device can have different compositions (e.g., different concentrations of solutes, such as proteins, carbohydrates, ions, or other molecules) which are in flux as solutes move down their respective concentration gradients and/or fluids flow through the device.

A microfluidic device or apparatus of the invention can comprise "swept" regions and "unswept" regions. An unswept region can be fluidically connected to a swept region, provided the fluidic connections are structured to enable diffusion but substantially no flow of media between the swept region and the unswept region. The microfluidic apparatus can thus be structured to substantially isolate an unswept region from a flow of medium in a swept region, while enabling substantially only diffusive fluidic communication between the swept region and the unswept region.

A colony of biological cells is "clonal" if all of the living cells in the colony that are capable of reproducing are daughter cells derived from a single parent cell. The term "clonal cells" refers to cells of the same clonal colony.

In some embodiments of the invention, biological activity in holding pens in a micro-fluidic device can be assayed by placing in the holding pens capture objects that bind a particular material of interest produced by the biological activity. The material of interest bound to each capture object can then be assessed in the micro-fluidic device. Embodiments of the invention can thus efficiently assay biological activity occurring in holding pens in a micro-fluidic device. Moreover, where the biological activity comprises clonal cell colonies each producing a particular biological material of interest in one of the holding pens, some embodiments of the invention can assess in the micro-fluidic device the ability of each colony to produce the material of interest while keeping each colony clonal (e.g., without mixing cells that can reproduce from any one colony with any another colony).

Figure 2A:
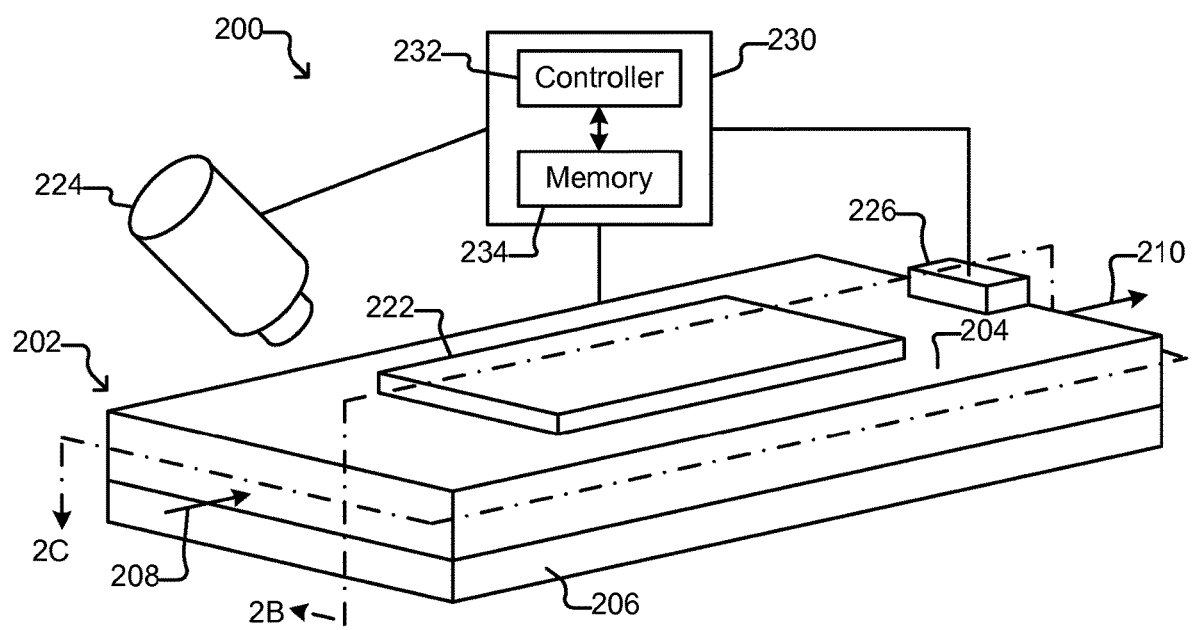
FIG. 2A is a perspective view of a micro-fluidic device with which the process of FIG. 1 can be performed according to some embodiments of the invention.
Figure 2B:
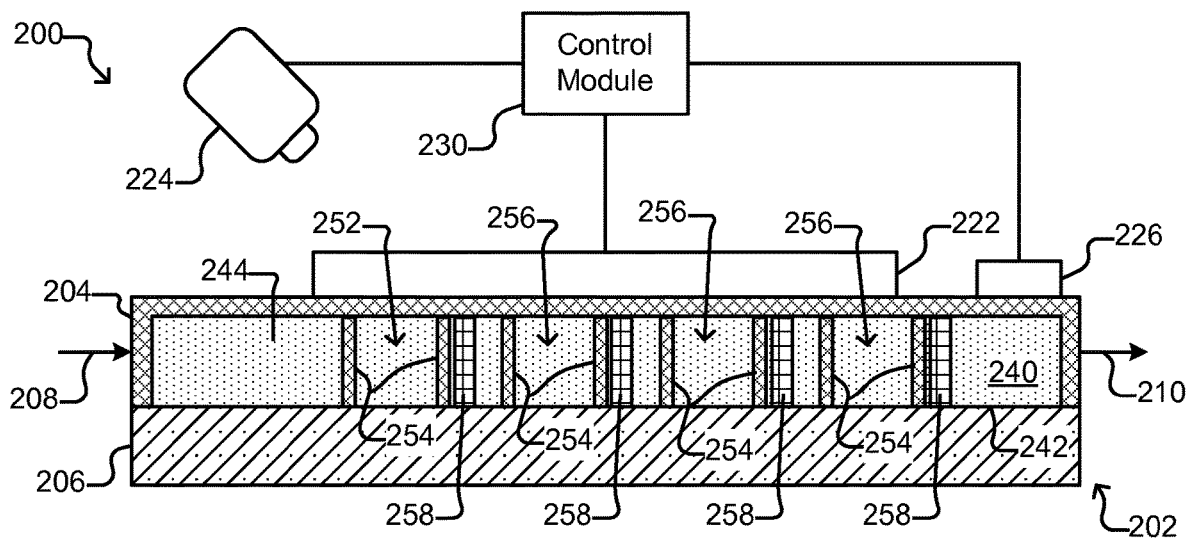
FIG. 2B is a side, cross-sectional view of the micro-fluidic device of FIG. 2A.
Figure 2C:
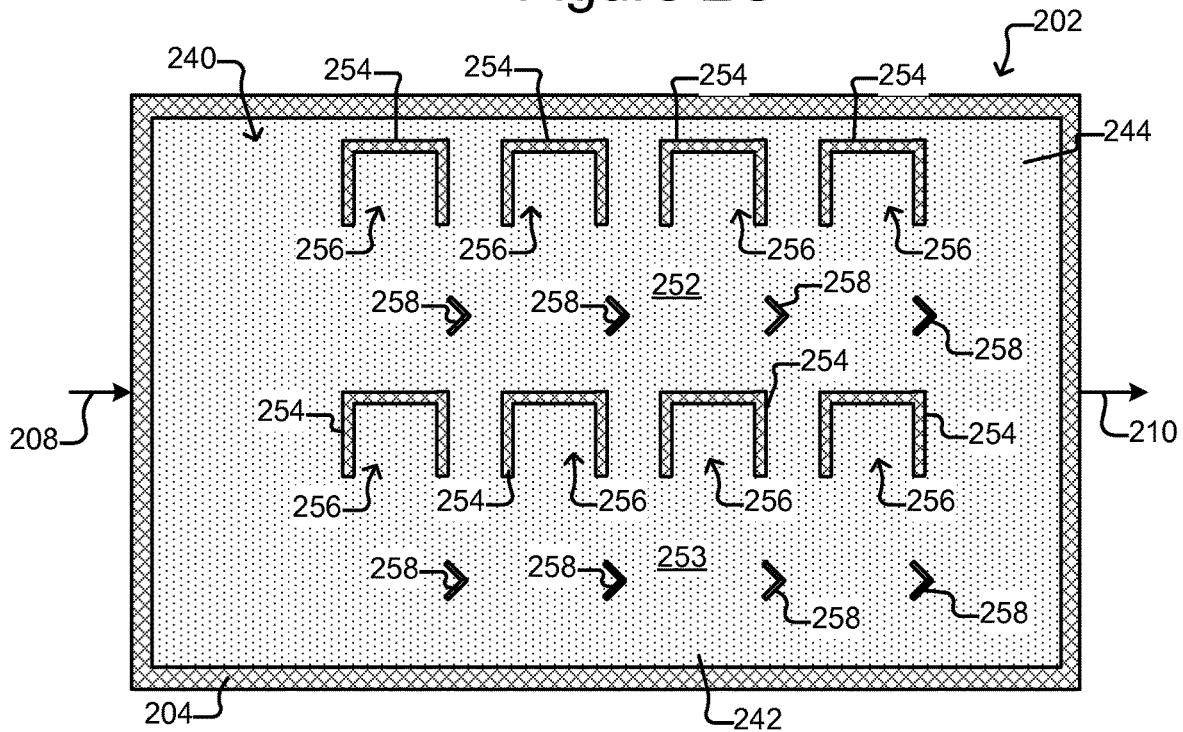
FIG. 2C is a top, cross-sectional view of the micro-fluidic device of FIG. 2A.
Figure 3A:
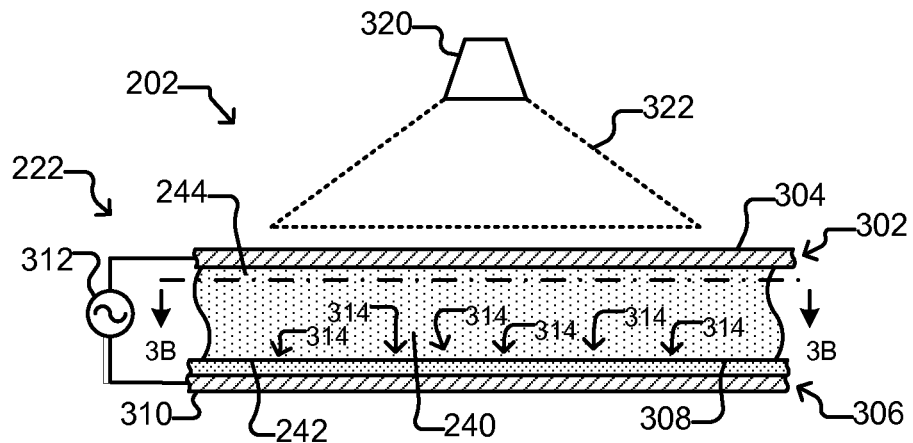
FIG. 3A is a partial side, cross-sectional view of the micro-fluidic device of FIGS. 2A-2C absent the barriers and stops (for ease of illustration) in which the selector is configured as a dielectrophoresis (DEP) device according to some embodiments of the invention.
Figure 3B:
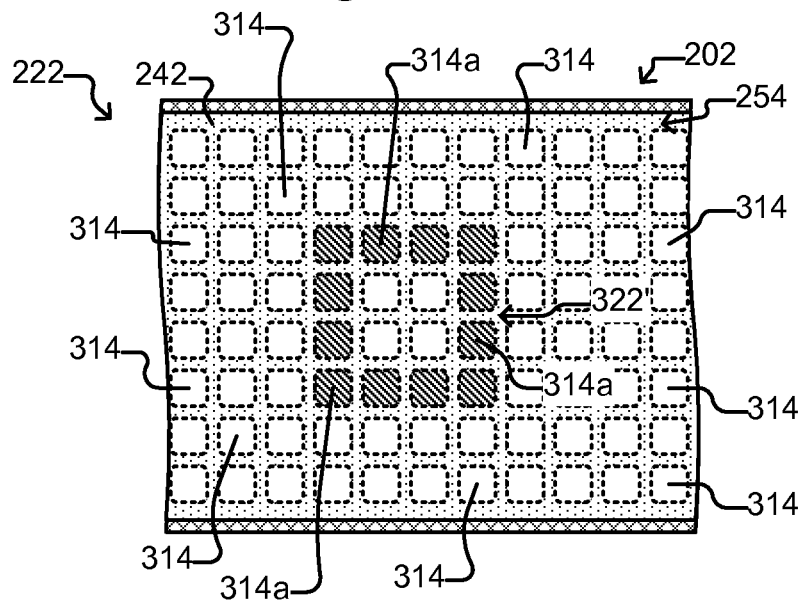
FIG. 3B is a partial top, cross-section view of FIG. 3A.

FIG. 1 illustrates an example of an assay process 100. FIGS. 2A-2C illustrate an example of a micro-fluidic device 200 for performing the process 100, and FIGS. 3A and 3B illustrate an example of a dielectrophoresis (DEP) device that can be part of the micro-fluidic device 200.

As shown in FIG. 1, at step 102, the process 100 can move capture objects into holding pens in a micro-fluidic device, and at step 104, the process 100 can culture a biological activity in each of the holding pens that produces a particular biological material of interest. The holding pens can include unswept regions, and the biological activity can be located in or placed into such an unswept region. The biological activity can be part of or consist of one or more cells, such as an, oocytes, sperms, cells dissociated from a tissue, blood cells (e.g., B cells, T cells, macrophages, and the like), hydridomas, cultured cells, cells from a cell line, cancer cells, infected cells, transfected and/or transformed cells, reporter cells, and the like. The capture objects can comprise one or more binding substances, each of which specifically binds to a particular biological material of interest. For example, a binding substance of a capture object can have an affinity (e.g., Kd) for a particular biological material of interest of at least about 1 mM or stronger (e.g., about 100 µM, 10 µM, 1 µM, 500 nM, 400 nM, 300 nM, 200 nM 100 nM, 75 nM, 50 nM, 25 nM, 15 nM, 10 nM, 5 nM, 2.5 nM, 1 nM, or stronger). Such affinity can be, for example, two, three, four, five, ten, or more times stronger than the affinity for any material other than the particular biological material of interest (or at least any other biological material of interest present in the holding pen and/or the microfluidic device). It can thus be said that each capture object binds one or more particular biological materials of interest but does not substantially bind other biological materials in the holding pens. After a time period, the capture objects can be removed from the holding pens at step 106, and a correlation between the removed capture objects and the pens from which each removed capture object was taken can be maintained at step 108. At step 110, biological activity in each holding pen can be assessed by analyzing the biological material bound to the capture object removed from the holding pen. For example, at step 110, the process 100 can rate the biological activity in each holding pen by determining the amount of biological material bound by a capture object removed for the holding pen. The rating can comprise, for example, a determination of whether the colony in each holding pen produces the material of interest at or above a threshold rate. As another example, the rating can quantify the amount of material of interest produced by the colony in each holding pen.

FIG. 1 is an example, and many variations of the process 100 are contemplated. For example, the process 100 can assess the biological activity at step 110 while the capture objects are in the holding pens, and process 100, in some variations, thus need not include steps 106, 108 or steps 106, 108 can be skipped. As another example, the steps 102-110 need not be performed in the order shown in FIG. 1. For example, steps 102 and 104 can be reversed.

FIGS. 2A-2C illustrate an example of a micro-fluidic device 200 on which the process 100 can be performed. As shown, the micro-fluidic device 200 can comprise a housing 202, a selector 222, a detector 224, a flow controller 226, and a control module 230.

As shown, the housing 202 can comprise one or more flow regions 240 for holding a liquid medium 244. FIG. 2B illustrates an inner surface 242 of the flow region 240 on which the medium 244 can be disposed as even (e.g., flat) and featureless. The inner surface 242, however, can alternatively be uneven (e.g., not flat) and comprise features such as electric terminals (not shown).

The housing 202 can comprise one or more inlets 208 through which the medium 244 can be input into the flow region 240. An inlet 208 can be, for example, an input port, an opening, a valve, another channel, fluidic connectors, or the like. The housing 202 can also comprise one or more outlets 210 through which the medium 244 can be removed. An outlet 210 can be, for example, an output port, an opening, a valve, a channel, fluidic connectors, or the like. As another example, the outlet 210 can comprise a droplet outputting mechanism such as any of the outputting mechanisms disclosed in U.S. patent application Ser. No. 13/856, 781 filed Apr. 4, 2013. All or part of the housing 202 can be gas permeable to allow gas (e.g., ambient air) to enter and exit the flow region 240.

The housing 202 can also comprise a micro-fluidic structure 204 disposed on a base (e.g., a substrate) 206. The micro-fluidic structure 204 can comprise a flexible material, such as rubber, plastic, an elastomer, silicone (e.g., patternable silicone), polydimethylsioxane ("PDMS"), or the like, which can be gas permeable. Alternatively, the micro-fluidic structure 204 can comprise other materials including rigid materials. The base 206 can comprise one or more substrates. Although illustrated as a single structure, the base 206 can comprise multiple interconnected structures such as multiple substrates. The micro-fluidic structure 204 can likewise comprise multiple structures, which can be interconnected. For example, the micro-fluidic structure 204 can additionally comprise a cover (not shown) made from material that is the same as or different than the other material in the structure.

The micro-fluidic structure 204 and the base 206 can define the flow region 240. Although one flow region 240 is shown in FIGS. 2A-2C, the micro-fluidic structure 204 and the base 206 can define multiple flow regions for the medium 244. The flow region 240 can comprise channels (252 and 253 in FIG. 2C) and chambers which can be interconnect to form micro-fluidic circuits. For enclosures that comprise more than one flow region 240, each flow region 240 can be associated with one or more inlets 208 and one or more outlets 210 for respectively inputting and removing medium 244 from the flow region 240.

As shown FIGS. 2B and 2C, holding pens 256 can be disposed in the flow region 240. For example, each holding pen 256 can comprise a barrier 254 that forms a partial enclosure. The partial enclosure can define non-flow spaces (or isolation regions). Thus, a portion of the interior of each holding pen 256 can be a non-flow space into which medium 244 from the channel 252 does not directly flow except when an empty flow region 240 is initially being filled with the medium 244. For example, each holding pen 256 can comprise one or more barriers 254 that form a partial enclosure the inside of which can include a non-flow space. The barriers 254 that define the holding pens 256 can thus prevent medium 244 from flowing directly into the protected interior of any of the holding pens 256 from the channel 252 while the flow region 240 is filled with medium 244. For example, a barrier 254 of a pen 256 can substantially prevent bulk flow of the medium 244 from the channel 252 into the non-flow spaces of the pens 256 while the flow region 240 is filled with medium 244, instead allowing substantially only diffusive mixing of medium from the channel 252 with medium in the non-flow space in a pen 256. Accordingly, exchange of nutrients and waste between the non-flow space in a holding pen 256 and the channel 252 can occur substantially only by diffusion.

The foregoing can be accomplished by orienting a pen 256 such that no opening into the pen 256 faces directly into the flow of medium 244 in a channel 252. For example, if the flow of medium is from the inlet 208 to the outlet 210 (and thus left to right) in the channel 252 in FIG. 2C, each of the pens 256 substantially impedes direct flow of medium 244 from the channel 252 into the pens 256 because the openings of each of the pens 256 do not face to the left in FIG. 2C, which would be directly into such a flow.

There can be many such holding pens 256 in the flow region 240 disposed in any pattern, and the holding pens 256 can be any of many different sizes and shapes. As shown in FIG. 2C, openings of the holding pens 256 can be disposed adjacent a channel 252, 253, which can be a space adjacent to the openings of more than one pen 256. The opening of each holding pen 256 can allow for the natural exchange of liquid medium 244 flowing in a channel 252, 253 but each holding pens 256 can otherwise be sufficiently enclosed to prevent micro-objects (not shown), such as biological cells, in any one pen 256 from mixing with micro-objects in any another pen 256. Although eight pens 256 and two channels 252, 253 are shown, there can be more or fewer. Medium 244 can be flowed in a channel 252, 253 past openings in the holding pens 256. The flow of medium 244 in channels 252, 253 can, for example, provide nutrients to biological objects (not shown) in the holding pens 256. As another example, the flow of medium 252, 253 in the common flow spaces 252, 253 can also provide for the removal of waste from the holding pens 256.

As shown in FIG. 2C, stops 258 can also be disposed in the flow region 240, for example, in the channels 252, 253. Each stop 258 can be configured to hold a micro-object (not shown) in place against a flow of the medium 244 in a channel 252, 253. The stops 258 and the barriers 254 of the pens 256 can comprise any of the types of materials discussed above with respect to the micro-fluidic structure 204. The stops 258 and barriers 254 can comprise the same material as the micro-fluidic structure 204 or a different material. The barriers 254 can extend from the surface 242 of the base 206 across the entirety of the flow region 240 to an upper wall (opposite the surface 242) of the microfluidic structure 204 as shown in FIG. 2B. Alternatively, one or more of the bathers 254 can extend only partially across the flow region 240 and thus not extend entirely to the surface 242 or the upper wall of the microfluidic structure 204. Although not shown, the stops 258 and/or the bathers 254 can include additional features such as one or more relatively small openings through which medium 244 can pass. Such openings (not shown) can be smaller than a micro-object (not shown) to prevent micro-objects from passing through.

The selector 222 can be configured to create selectively electrokinetic forces on micro-objects (not shown) in the medium 244. For example, the selector 222 can be configured to selectively activate (e.g., turn on) and deactivate (e.g., turn off) electrodes at the inner surface 242 of the flow region 240. The electrodes can create forces in the medium 244 that attract or repel micro-objects (not shown) in the medium 244, and the selector 222 can thus select and move one or more micro-objects in the medium 244. The electrodes can be, for example, dielectrophoresis (DEP) electrodes.

For example, the selector 222 can comprise one or more optical (e.g., laser) tweezers devices and/or one or more optoelectronic tweezers (OET) devices (e.g., as disclosed in U.S. Pat. No. 7,612,355 (which is incorporated in its entirety by reference herein) or U.S. patent application Ser. No. 14/051,004 (which is also incorporated in its entirety by reference herein). As yet another example, the selector 222 can include one or more devices (not shown) for moving a droplet of the medium 244 in which one or more of micro-objects are suspended. Such devices (not shown) can include electrowetting devices such as optoelectronic wetting (OEW) devices (e.g., as disclosed in U.S. Pat. No. 6,958,132) or other electrowetting devices. The selector 222 can thus be characterized as a DEP device in some embodiments.

FIGS. 3A and 3B illustrate an example in which the selector 222 comprises an OETa DEP device 300. As shown, the DEP device 300 can comprise a first electrode 304, a second electrode 310, an electrode activation substrate 308, a power source 312 (e.g., an alternating current (AC) power source), and a light source 320. Medium 244 in the flow region 240 and the electrode activation substrate 308 can separate the electrodes 304, 310. Changing patterns of light 322 from the light source 320 can selectively activate and deactivate changing patterns of DEP electrodes at regions 314 of the inner surface 242 of the flow region 240. (Hereinafter the regions 314 are referred to as "electrode regions.")

In the example illustrated in FIG. 3B, a light pattern 322' directed onto the inner surface 242 illuminates the cross-hatched electrode regions 314a in the square pattern shown. The other electrode regions 314 are not illuminated and are hereinafter referred to as "dark" electrode regions 314. The relative electrical impedance across the electrode activation substrate 308 from each dark electrode region 314 to the second electrode 310 is greater than the relative impedance from the first electrode 304 across the medium 244 in the flow region 240 to the dark electrode region 314. Illuminating an electrode region 314a, however, reduces the relative impedance across the electrode activation substrate 308 from the illuminated electrode region 314a to the second electrode 310 to less than the relative impedance from the first electrode 304 across the medium 244 in the flow region 240 to the illuminated electrode region 314a.

With the power source 312 activated, the foregoing creates an electric field gradient in the medium 244 between illuminated electrode regions 314a and adjacent dark electrode regions 314, which in turn creates local DEP forces that attract or repel nearby micro-objects (not shown) in the medium 244. DEP electrodes that attract or repel micro-objects in the medium 244 can thus be selectively activated and deactivated at many different such electrode regions 314 at the inner surface 242 of the flow region 240 by changing light patterns 322 projected form a light source 320 (e.g., a laser source, a high intensity discharge lamp, or other type of light source) into the micro-fluidic device 200. Whether the DEP forces attract or repel nearby micro-objects can depend on such parameters as the frequency of the power source 312 and the dielectric properties of the medium 244 and/or micro-objects (not shown).

The square pattern 322' of illuminated electrode regions 314a illustrated in FIG. 3B is an example only. Any pattern of the electrode regions 314 can be illuminated by the pattern of light 322 projected into the device 200, and the pattern of illuminated electrode regions 322' can be repeatedly changed by changing the light pattern 322.

In some embodiments, the electrode activation substrate 308 can be a photoconductive material, and the inner surface 242 can be featureless. In such embodiments, the DEP electrodes 314 can be created anywhere and in any pattern on the inner surface 242 of the flow region 240 in accordance with the light pattern 322 (see FIG. 3A). The number and pattern of the electrode regions 314 are thus not fixed but correspond to the light pattern 322. Examples are illustrated in the aforementioned U.S. Pat. No. 7,612,355, in which the un-doped amorphous silicon material 24 shown in the drawings of the foregoing patent can be an example of photoconductive material that can compose the electrode activation substrate 308.

In other embodiments, the electrode activation substrate 308 can comprise a circuit substrate such as a semiconductor material comprising a plurality of doped layers, electrically insulating layers, and electrically conductive layers that form semiconductor integrated circuits such as is known in semiconductor fields. In such embodiments, electric circuit elements can form electrical connections between the electrode regions 314 at the inner surface 242 of the flow region 240 and the second electrode 310 that can be selectively activated and deactivated by the light pattern 322. When not activated, each electrical connection can have high impedance such that the relative impedance from a corresponding electrode region 314 to the second electrode 310 is greater than the relative impedance from the first electrode 204 through the medium 244 to the corresponding electrode region 314. When activated by light in the light pattern 322, however, each electrical connection can have low impedance such that the relative impedance from a corresponding electrode region 314 to the second electrode 310 is less than the relative impedance from the first electrode 304 through the medium 244 to the corresponding electrode region 314, which activates a DEP electrode at the corresponding electrode region 314 as discussed above. DEP electrodes that attract or repel micro-objects (not shown) in the medium 244 can thus be selectively activated and deactivated at many different electrode regions 314 at the inner surface 242 of the flow region 240 by the light pattern 322. Non-limiting examples of such configurations of the electrode activation substrate 308 include the phototransistor-based OET device 300 illustrated in FIGS. 21 and 22 of U.S. Pat. No. 7,956,339 and the OET devices illustrated throughout the drawings in the aforementioned U.S. patent application Ser. No. 14/051,004.

In some embodiments, the first electrode 304 can be part of a first wall 302 (or cover) of the housing 202, and the electrode activation substrate 308 and second electrode 310 can be part of a second wall 306 (or base) of the housing 202 generally as illustrated in FIG. 3A. As shown, the flow region 240 can be between the first wall 302 and the second wall 306. The foregoing, however, is but an example. In other embodiments, the first electrode 304 can be part of the second wall 306 and one or both of the electrode activation substrate 308 and/or the second electrode 310 can be part of the first wall 302. As another example, the first electrode 304 can be part of the same wall 302 or 306 as the electrode activation substrate 308 and the second electrode 310. For example, the electrode activation substrate 308 can comprise the first electrode 304 and/or the second electrode 310. Moreover, the light source 320 can alternatively be located below the housing 202.

Configured as the DEP device 300 of FIGS. 3A and 3B, the selector 222 can thus select a micro-object (not shown) in the medium 244 in the flow region 240 by projecting a light pattern 322 into the device 200 to activate one or more DEP electrodes at electrode regions 314 of the inner surface 242 of the flow region 240 in a pattern that surrounds and captures the micro-object. The selector 222 can then move the captured micro-object by moving the light pattern 322 relative to the device 200. Alternatively, the device 200 can be moved relative to the light pattern 322.

Although the barriers 254 that define the holding pens 256 are illustrated in FIGS. 2B and 2C and discussed above as physical barriers, the barriers 254 can alternatively be virtual barriers comprising DEP forces activated by the light pattern 322. The stops 258 can likewise comprise physical barriers and/or virtual barriers comprising DEP forces activated by the light pattern 322.

With reference again to FIGS. 2A-2C, the detector 224 can be a mechanism for detecting events in the flow region 240. For example, the detector 224 can comprise a photodetector capable of detecting one or more radiation characteristics (e.g., due to fluorescence or luminescence) of a micro-object (not shown) in the medium. Such a detector 224 can be configured to detect, for example, that one or more micro-objects (not shown) in the medium 244 are radiating electromagnetic radiation and/or the approximate wavelength, brightness, intensity, or the like of the radiation. Examples of suitable photodetectors include without limitation photomultiplier tube detectors and avalanche photodetectors.

The detector 224 can alternatively or in addition comprise an imaging device for capturing digital images of the flow region 240 including micro-objects (not shown) in the medium 244. Examples of suitable imaging devices that the detector 224 can comprise include digital cameras or photosensors such as charge coupled devices and complementary metal-oxide-semiconductor imagers. Images can be captured with such devices and analyzed (e.g., by the control module 230 and/or a human operator).

The flow controller 226 can be configured to control a flow of the medium 244 in the flow region 240. For example, the flow controller 226 can control the direction and/or velocity of the flow. Non-limiting examples of the flow controller 226 include one or more pumps or fluid actuators. In some embodiments, the flow controller 226 can include additional elements such as one or more sensors (not shown) for sensing, for example, the velocity of the flow of the medium 244 in the flow region 240.

The control module 230 can be configured to receive signals from and control the selector 222, the detector 224, and/or the flow controller 226. As shown, the control module 230 can comprise a controller 232 and a memory 234. In some embodiments, the controller 232 can be a digital electronic controller (e.g., a microprocessor, microcontroller, computer, or the like) configured to operate in accordance with machine readable instructions (e.g., software, firmware, microcode, or the like) stored as non-transitory signals in the memory 234, which can be a digital electronic, optical, or magnetic memory device. Alternatively, the controller 232 can comprise hardwired digital circuitry and/or analog circuitry or a combination of a digital electronic controller operating in accordance with machine readable instructions and hardwired digital circuitry and/or analog circuitry.

As mentioned, the micro-fluidic device 200 is an example of a device that can be used to perform the process 100. For example, at step 102, the selector 222 (e.g., configured as shown in FIGS. 3A and 2B) can select capture objects (not shown) in the medium 244 in the flow region 240 and move the selected capture objects into holding pens 256. At step 104, nutrients can be provided to biological micro-objects (not shown) in the pens 256 in flows of the medium 244 in the channels 252, 253. At step 106, the selector 222 can select and remove capture objects (not shown) from the pens 256, and at step 108, the detector 224 and controller 230 can correlate each removed capture object (not shown) with the pen 256 from which the capture object was taken. For example, the detector 224 can capture images of the capture objects (not shown) and pens 256, and the controller 230 can store the correlation as digital data in the memory 234. At step 110, the biological material bound to each removed capture object (not shown) can be assessed in the microfluidic device 200. For example, the detector 224 can capture images or detect characteristics of the removed capture objects (not shown) to assess the biological material bound to the removed capture objects.

FIG. 4 illustrates another example of a process 400 for assaying biological activity in holding pens of a microfluidic device. The process 400 can be a narrower example of the more general process 100 in which, in the process 400 of FIG. 4, the biological activity in the holding pens is production of a biological material of interest by clonal colonies of cells. For ease of illustration and discussion, process 400 is discussed below with respect to the microfluidic device 200 of FIGS. 2A-2C in which the selector 222 can be configured as illustrated in FIGS. 3A and 3B. The process 400 is not so limited, however, and can thus be performed on other micro-fluidic devices.

Figure 5A:
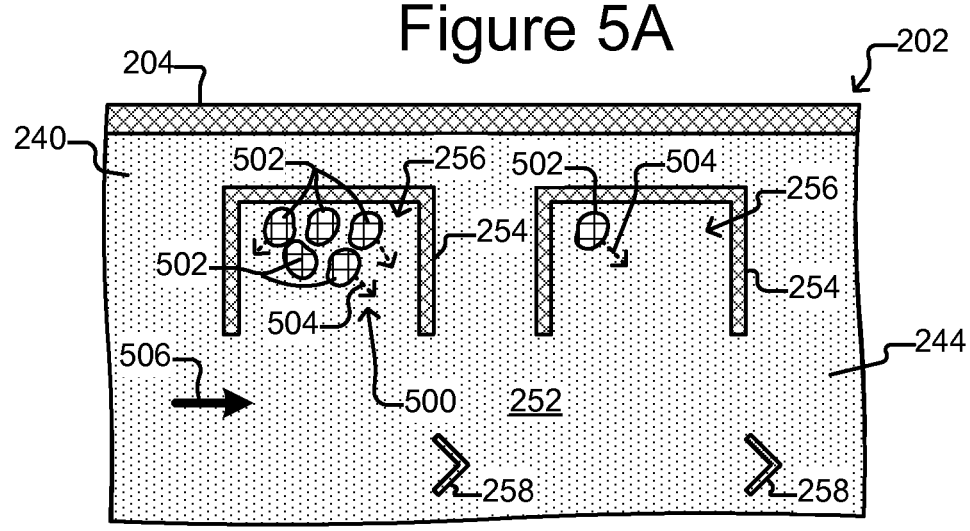
FIG. 5A illustrates an example of the culturing step of FIG. 4 according to some embodiments of the invention.

As shown in FIG. 4, at step 402, the process 400 can culture production of colonies of clonal cells in holding pens 256 of a micro-fluidic device 200. FIG. 5A (which, like FIGS. 6, 7A, 8-11B, and 12-14 shows a top, cross-sectional view of a portion of the flow region 240 of the micro-fluidic device 200 of FIGS. 2A-2C) and FIG. 5B illustrate examples.

Figure 5B:
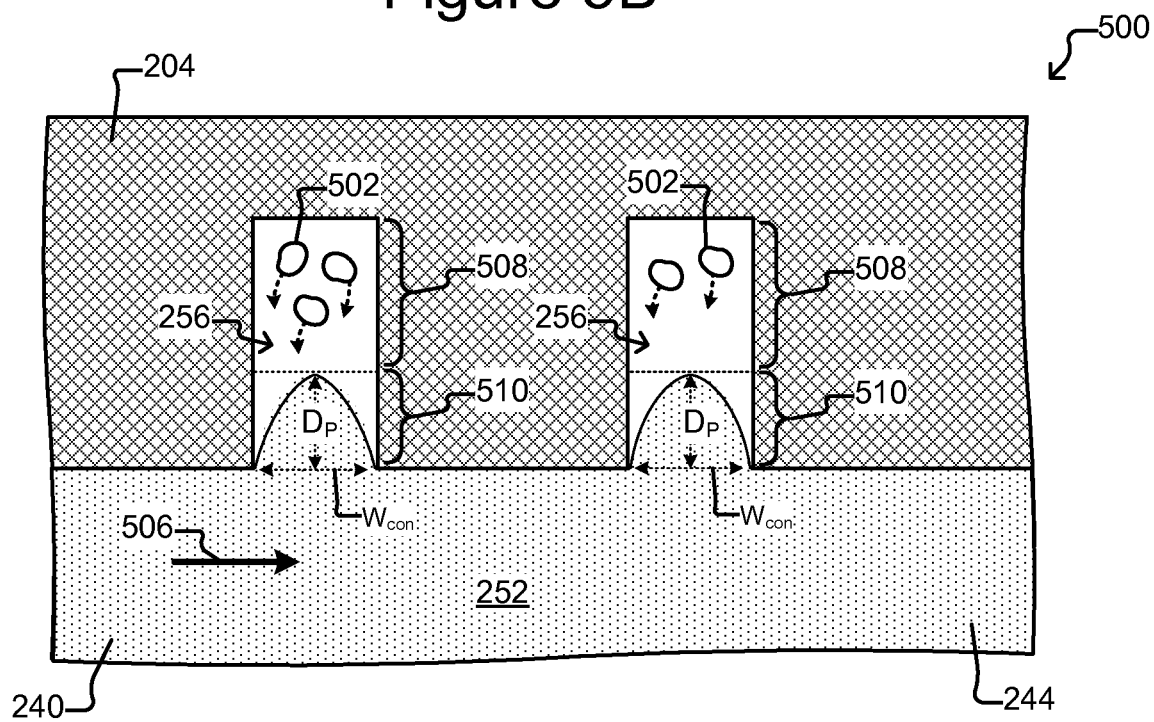
FIG. 5B illustrates an example of the culturing step of FIG. 4 in which the biological cells are cultured in holding pens that have an isolation region and a connection region.

As shown in FIGS. 5A and 5B, biological cells 502 can be cultured in one or more of the holding pens 256 by flowing 506 liquid medium 244 in a channel 252 adjacent the openings of at least some of the pens 256. Nutrients in the flow 506 can culture the biological activity in the holding pens 256. The flow 506 can also provide removal of waste from the pens 256. A similar flow can be provided in other channels (e.g., 253 shown in FIG. 2C) adjacent the openings of other pens 256 in the device 200.

FIG. 5B shows pens having isolation regions 508 and connection regions 510. As is known, a flow 506 of fluidic medium 244 in a microfluidic channel 252 past a proximal opening of a pen 256 can cause a secondary flow of the medium 244 into and/or out of the pen. To isolate micro-objects 502 in the isolation region 508 of a pen 256 from the secondary flow, the length of the connection region 510 of the sequestration pen 256 from the proximal opening to the distal opening can be greater than a maximum penetration depth $D_p$ of the secondary flow into the connection region 510 when the velocity of the flow 506 in the channel 252 is at a maximum ($V_{max}$). As long as the flow 506 in the channel 252 does not exceed the maximum velocity $V_{max}$, the flow 506 and resulting secondary flow can thus be limited to the channel 252 and the connection region 510 and kept out of the isolation region 508. The flow 506 in the channel 252 will thus not draw biological micro-objects 502 (or any other micro-objects) out of the isolation region 508. Bilogical micro-objects 502 in the isolation region 508 will thus stay in the isolation region 508 regardless of the flow 506 in the channel 252.

The culturing at step 402 can facilitate multiplication of the cell or cells 502 in each pen 256 to produce a colony 500 of cells 502 in each pen 256. Each pen 256 can isolate its cells 502 from the cells 502 in all of the other pens 256 sufficiently to prevent cells 502 in any one pen 256 from mixing with cells 502 in any another pen 256. Moreover, the colony 500 produced in each holding pen 256 can start with a single cell 502 in the pen 256. The colony 500 of cells 502 in each pen 256 can thus be clonal.

Culturing at step 402 can also facilitate production of a particular material of interest 504 that is to be assayed. Non-limiting examples of the material of interest 504 include proteins, nucleic acids, carbohydrates, lipids, hormones, metabolites, or any combination thereof. Proteins of interest may include, for example, therapeutic proteins, antibodies, growth factors, cytokines, cancer cell-specific antigens, antigens associated with a virus or other pathogen, secreted proteins, or any other proteins produced and/or released by biological cells. Thus, for example, the cells 502 can be protein (e.g., antibody) producing cells, and the material of interest 504 can be a particular protein (e.g., a particular antibody). For example, the material of interest can be the antibody of the immunoglobulin G (IgG) isotype. Material, including biological material, other than the material of interest 504 can be in the pens. For example, the cells 502 can produce, in addition to the material of interest 504, other materials.

In some embodiments, culturing at step 402 can involve multiple types of culturing. For example, a first flow 506 of a first type of medium 244 can culture growth and division of the cells 502 in each pen 256. Thereafter, a second flow of a second type of medium 244 can culture production of the material of interest 504 by the cells 502 in each pen 256.

Figure 7B:
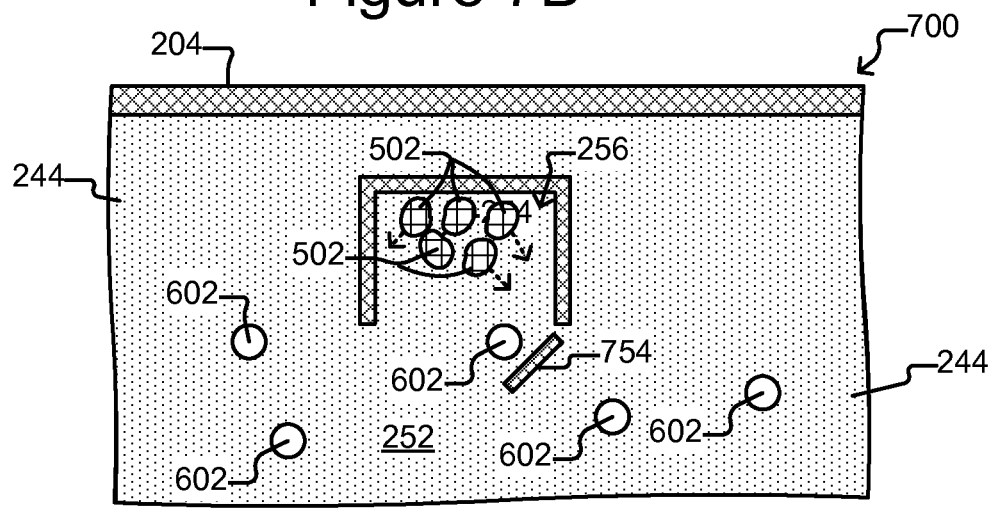
FIG. 7B illustrates a variation of the micro-fluidic device of FIG. 7A in which a deflector is used to guide capture objects into a holding pen as they flow through a channel to which the holding pen is adjacent.
Figure 8:
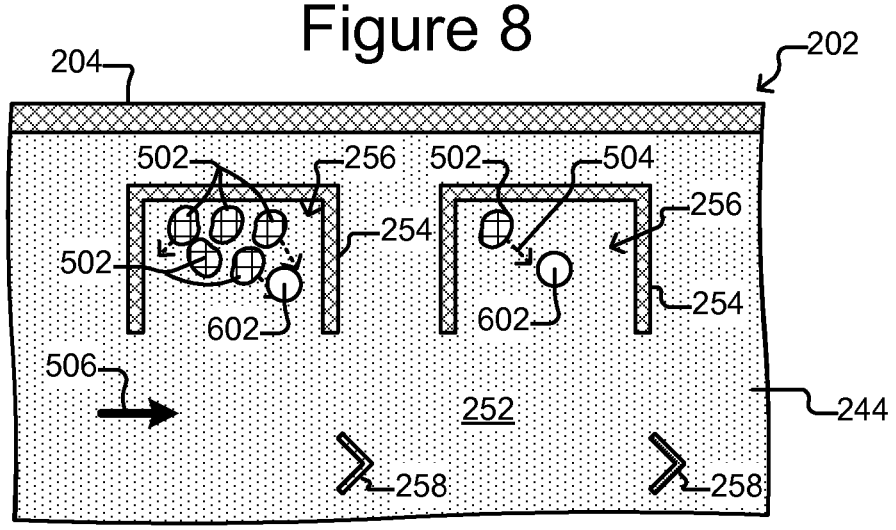
FIGS. 8 and 9 show an example of the step of continuing to culture in FIG. 4 according to some embodiments of the invention.

At step 404 of FIG. 4, the process 400 can move capture objects 602 into the holding pens 256. The capture objects 602 can be, for example, inanimate micro-objects such as microparticles, microbeads (e.g., polystyrene beads, Luminex™ beads, or the like), magnetic beads, microrods, microwires, quantum dots, or the like. In some cases, the capture objects 602 can be a combination of inanimate micro-objects and biological micro-objects (e.g., liposome-coated micro-beads, liposome-coated magnetic beads, microbeads attached to cells, or the like). In still other cases, capture objects 602 can be biological micro-objects such as cells, liposomes, lipid nanorafts, or the like. Moreover, each capture object 602 can comprise a particular binding substance that that specifically binds a particular biological material of interest. The capture object 602 can comprise a particular binding substance that, e.g., has an affinity (e.g., Kd) for a particular biological material of interest of at least about 1 mM or stronger (e.g., about 100 µM, 10 µM, 1 µM, 500 nM, 400 nM, 300 nM, 200 nM 100 nM, 75 nM, 50 nM, 25 nM, 15 nM, 10 nM, 5 nM, 2.5 nM, 1 nM, or stronger). Such affinity can be, for example, two, three, four, five, ten, or more times stronger than the affinity for any material other than the particular biological material of interest (or at least any other biological material of interest present in the holding pen and/or the microfluidic device) For example, if the material of interest 504 is a particular antibody, the capture objects 602 can comprise a binding substance (e.g., an antigen or epitope thereof) that has greater affinity for that particular antibody than for any other material in the holding pen 256 and/or the microfluidic device. As noted, the material of interest 504 can be an IgG antibody, in which case, the binding substance of the capture objects 602 can comprise a material with an IgG Fc receptor for binding IgG antibodies. FIGS. 6-8 illustrate an example of step 404.

As shown in FIG. 6, capture objects 602 can be disposed in the channel 252 adjacent openings to pens 256. As shown in FIGS. 7A-7B and 8, individual capture objects 602 can be moved into specific pens 256.

The capture objects 602 can be introduced into the micro-fluidic device 200 through the inlet 208 (see FIGS. 2A-2C) and moved with the flow 506 to the channel 252 as shown in FIG. 6. FIG. 7A illustrates an example in which the selector 222 (see FIGS. 2A-2C) configured like the DEP device 300 of FIGS. 3A-3B generates a light trap 702 that can trap an individual capture object 602. The DEP device 300 can then move the light trap 702 into one of the pens 256, which moves the trapped capture object 602 into the pen 256. The light trap 702 can be part of a changing pattern 322 of light projected onto an inner surface 242 of the flow region 240 of the micro-fluidic device 200 as discussed above with respect to FIGS. 3A and 3B. Once a capture object 602 is in a pen 256, the light trap 602 corresponding to that capture object 602 can be turned off as illustrated in FIG. 8. The detector 224 can capture images of all or part of the flow region 240, and those images can facilitate trapping and moving individual capture objects 602 into specific pens 256. Thus, a specific number (e.g., one or more) of the capture objects 602 can be identified, selected, and moved into each pen 256.

As shown in FIG. 7A, the flow 506 of medium 244 can be stopped after the flow 506 brings capture objects 602 into the channel 252. Stopping the flow 506 can facilitate identifying and selecting individual capture objects 602. As shown in FIG. 8, once the capture objects 602 are in the pens 256, the flow 506 can be resumed. Alternatively, rather than stop the flow 506, the flow 506 can merely be slowed to a velocity that is sufficiently slow for the detector 224 to detect and the selector 222 to trap and move individual capture objects 602 in the channel 252. As yet another alternative, the flow 506 can be started and maintained at a generally steady rate that is slow enough for the detector 224 to detect and the selector 22 to trap and move individual capture objects 602. In such a case, the flow 506 can be maintained at a generally constant velocity in each of FIGS. 6, 7A, and 8.

Although FIG. 7A illustrates trapping one capture object 602 per trap 702, a trap 702 can capture more than one capture object 602. Similarly, although FIG. 8 shows one capture object 602 in each pen 256, more than one capture object 602 can be moved into a pen 256. Regardless, a specific, known number of capture objects 602 (e.g., one or more) can be moved into each pen 256. Generally speaking, the order of steps in the processes 100 and 400 is not critical, and thus, for example, the order of steps 404 and 402 can be reversed. For example, capture objects 602 can be placed in the holding pens 256 before even a first cell 502 is placed in the pens 256. In such cases, the process can include a step for moving biological activity (e.g., biological cells 502) into the holding pens 256.

As an alternative to actively selecting and moving capture objects 602 into the holding pens 256, FIG. 7B illustrates a more passive approach to loading capture objects 602 into the holding pens 256. The micro-fluidic device of FIG. 7B is similar to that shown in FIG. 7A, except that there is a deflector 754 located in the channel 252, just outside of the holding pen 256. When capture objects 602 are flowed into the micro-fluidic device and through the channel 252, a small fraction of the capture objects 602 will be carried to the periphery of the channel 252. Capture objects 602 being carried by the flow 506 at the periphery of the channel 252 can be caught by the deflector 754 and deflected into the holding pen 256. Unlike the approach that uses a light trap to select and move specific capture objects 602 into specific holding pens 256, the use of a deflector as shown in FIG. 7B does not allow for careful control of exactly which capture objects 602 or how many capture objects 602 are moved into each holding pen 256. However, the use of a deflector 754 can facilitate the loading of large numbers of holding pens simultaneously.

The deflector 754 shown in FIG. 7B can be made of the same material as bather 254, or any other suitable material discussed herein. In addition, the deflector 754 can be separate from the barrier 254 (as shown) or attached. The deflector 754 extend the full height of the channel 252, or it can extend only partly up through the channel, thereby potentially reducing the number of capture objects 602 (or biological micro-objects, such as cells) that get deflected into holding pen 256. Moreover, deflector 754 can be a virtual barrier created by light focused on the surface of the 242 of the channel 252. Such light can activate electrodes (e.g., DEP electrodes), thereby creating a barrier to capture objects 602 (or cells 502) in the manner of the light traps discussed above. Such virtual deflectors can be advantageous because they can be turned off once a threshold number of capture objects 602 have been deflected into the holding pen 256. For example, a human user or the controller 230 can monitor the number of capture objects 602 deflected into any particular holding pen 256 and then turn off the light that is activating the electrodes (and thereby generating the deflector) once the threshold number of capture objects 602 is reached.

As yet another alternative to actively selecting and moving capture objects 602 into the holding pens 256, a high rate of flow 506 of medium 244 in channel 252 can be used to increase the penetration depth Dp of secondary flow entering the holding pens 256. Thus, by increasing the rate of flow 506 of medium 244 in the channel 252, capture objects 602 can be pushed into holding pens 256. In some embodiments, the micro-fluidic device has a channel 252 having a cross-sectional area of about 3,000 to 6,000 square microns, or about 2,500 to 4,000 square microns. The rate of flow 506 of medium 244 suitable for loading capture objects 602 into holding pens 256 is such a micro-fluidic device can be, e.g., about 0.05 to 5.0 µL/sec (e.g., about 0.1 to 2.0, 0.2 to 1.5, 0.5 to 1.0 µL/sec, or about 1.0 to 2.0 µL/sec).

Figure 9:
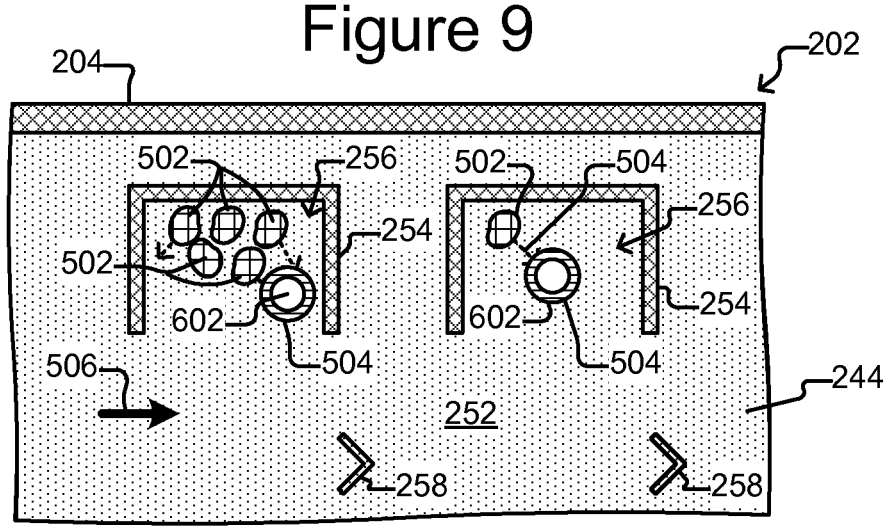

At step 406 of FIG. 4, culturing the cells 502 in the pens 256 can continue for a time period during which the cells 502 can continue to multiply and/or produce the material of interest 504. As illustrated in FIG. 9, the capture objects 602 in a particular pen 256 can bind material of interest 504 produced by the cells 502 in that pen 256. FIG. 9 thus shows material of interest 504 bound to the capture objects 602 in the pens 256.

In some embodiments, the purpose of the assay process 400 of FIG. 4 can be to identify cell colonies 502 in the pens 256 that produce the material of interest 504 at a minimum threshold rate. In such embodiments, the amount of material of interest 504 that the one or more capture objects 602 in any one pen 256 can bind and the time period of step 406 can be such that a colony 500 producing the material of interest 504 at or above the minimum threshold rate will produce enough material of interest 504 to saturate the capture object(s) 602 in the pen 256.

In other embodiments, the purpose of the assay process 400 can be to determine the quantity of the material of interest 504 produced in each pen 256. In such embodiments, the amount of material of interest 504 that the one or more capture objects 602 in a pen 256 can bind and the time period of step 406 can be such that a colony 500 producing the material of interest 504 even at a highest possible rate would not saturate the capture object(s) 602 in the pen 256.

As illustrated in the holding pen 256 on the right of the page in FIGS. 5-14, the process 400 can assay a single biological object 502 (e.g., a single biological cell) in a holding pen 256. The ability to assay a single biological object 502 in a holding pen 256 is significant because it is believed that known techniques for assaying biological cells, for example, are not sensitive enough to assay, for example, material produced by a single cell.

Figure 10:
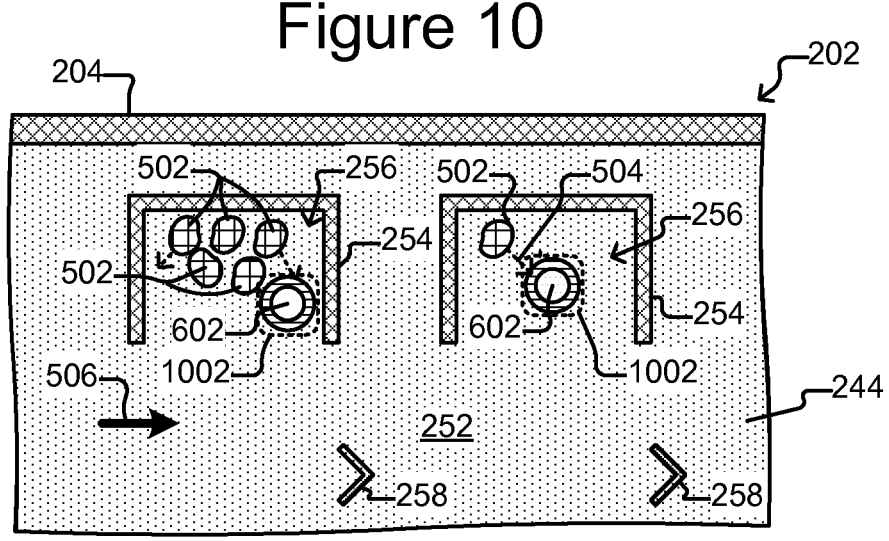
FIG. 10 illustrates an example of the removing step of FIG. 4 according to some embodiments of the invention.

As illustrated in FIG. 4, after the time period of step 406 discussed above, at step 408, the process 400 can select individual capture objects 602 from specific pens 256 and remove the selected capture objects 602 from the pens 256. In some embodiments, the removed capture objects 602 can be moved into the channel 252. FIGS. 10 and 11A show an example of step 408.

As shown in FIG. 10, an individual capture object 602 can be selected in a specific pen 256 with a light trap 1002, which can be like the light trap 702 discussed above. As shown in FIG. 11A, trapped capture objects 602 can be removed from a pen 256 and placed in the channel 252 adjacent an opening of the pen 256. For example, the light trap 1002 can be moved from the pen 256 into the channel 252. As also shown in FIG. 11A, a capture object 602 can be moved to a stop 258 in the channel 252, which as discussed, can hold the capture object 602 in place against the flow 506 of medium 244 in the flow region 240. Once a removed capture object 602 is moved to a stop 258, the light trap 1002 can turned off. Alternatively, the light trap 1002 can be kept on to hold the removed capture object 602 in place, for example, against the flow 506 of medium 244. In such a case, the stops 258 need not be included in the flow region 240 of the device 200. Regardless, the flow 506 can be slowed or even stopped during step 408. As yet another alternative, the capture object 602, once moved into the channel 252, can be exported from the device for subsequent analysis. Suitable methods for exporting capture objects are disclosed, for example, in U.S. patent application Ser. No. 14/520,150, filed Oct. 22, 2014, the entire contents of which are incorporated herein by reference. The capture object 602 can be exported individually, with a group of capture objects from the same holding pen 256, or with a group that includes capture objects 602 from a plurality of holding pens 256. In the latter case, the capture objects 602 can have identifiers that facilitate their identification and association with the holding pen 256 from which they were removed. For example, Luminex™ beads can be used as capture objects 602, thereby allowing capture objects 602 from a specific holding pen 256 to be distinguished from capture objects from other holding pens 256.

As shown in FIG. 11B, an alternative to moving the capture object 602 to a stop 258 in channel 252 involves moving the capture object 602 to an assay region 1156. The assay region 1156 can be adjacent to holding pen 256, thereby reducing the time required to move the capture object 602 and facilitating maintenance of a correlation between the capture object 602 and the holding pen 256 from which it has been removed. The assay region can be defined by a barrier 1154, which can be made of the same material as barrier 254, or any other suitable material discussed herein. Although shown as having the same size and shape as holding pen 256, the assay region 1156 can be smaller and/or have a different shape. For example, the assay region 1156 can be smaller and may or may not include an isolation region. Thus, for example, the assay region 1156 can substantially lack an isolation region (e.g., less than 50% of the volume of assay region can be isolated from secondary flow of the flow 506 of medium 244 in the channel 25). The substantially lack of an isolation region can, in certain embodiments, facilitate washing of assay materials away from the capture object 602 (discussed further below).

As an alternative to using a light trap 1002 to move the capture object 602 out of holding pen 256, a magnetic capture object 602 can be forced out of pen 256 using a magnetic force, such as a magnet. As shown in FIG. 11C, the micro-fluidic device 1100 can include assay regions 1156 located across channel 252 from the openings to holding pens 256. To move magnetic capture objects 602 out of the holding pens 256 and into the assay regions 1156, a magnetic force can be applied to the micro-fluidic device such that the magnetic capture objects 602 are either pulled or pushed into the assay regions 1156. During such as step, the flow 506 of medium 244 in the channel 252 can be slowed or stopped.

Although one capture object 602 is shown in FIGS. 10 and 11A-11C being removed from each pen 256, as mentioned above, more than one capture object 602 can be placed into a pen 256 at step 404, and in such a case, more than one capture object 602 can accordingly be removed from a pen 256 at step 408.

Returning again to FIG. 4, at step 410, the process 400 can maintain correlation between each capture object 602 removed from a pen 256 at step 408 and the pen 256 from which the capture object 602 was removed. For example, the controller 232 can identify and track locations of capture objects 602 and pens 256 from images provided by the detector 224, and the controller 232 can store in the memory 234 a correlation between individual removed capture objects 602 in the channel 252 and the pens 256 from which each capture object 602 was taken. Table 1 is an example of a digital table that can be stored in the memory 234, which correlates the locations in the channel 252 of the capture objects 602 to the pens 256 from which the capture objects 602 were removed. In the example of Table 1, the capture object 602 at stop 258 identified as stop A was taken from a pen 256 numbered three. Similarly, the capture object 602 at stop 258B was taken from a pen 256 numbered one, and the capture object 602 at stop 258C was taken from a pen 256 numbered two. A corresponding table could be used to store data regarding the location of capture objects 602 in assay regions 1156 and the holding pens 256 from which the capture objects 602 were removed. Similarly, for capture objects 602 that are exported from the micro-fluidic device for analysis, a table can be used to store data regarding the identifiers associated with specific capture objects 602 and the holding pens 256 from which such capture objects 602 were removed.

TABLE 1

| Capture Object Location | Pen |
| --- | --- |
| Stop A | Pen 3 |
| Stop B | Pen 1 |
| Stop C | Pen 2 |

At step 412 of FIG. 4, the process 400 can assess the material of interest 504 bound to the removed capture objects 602 in the channel 252. For example, the process 400 can assess at step 412 the material of interest 504 by determining the quantity and/or the quality of the material of interest 504 produced by a colony 500 of cells or a single cell 502 in a pen 256. As another example, the process 400 can assess at step 412 the type of material 504 produced by a colony 500 of cells 502 or a single call 502 in a pen 256. As yet another example, the process 400 can assess at step 412 an activity of the material 504 produced by a colony 500 of cells 502 or a single cell 502 in a pen 256. Because the material of interest 504 bound to a capture object 602 was produced by the biological activity in the pen 256 from which the capture object 602 was removed at step 408, the assessment of the material of interest 504 bound to a removed capture object 602 at step 412 can provide information from which the biological activity in the pen 256 can be assessed. FIGS. 12-14 illustrate an example of step 412.

As shown in FIG. 12, at step 412, an assay material 1202 can be flowed 506 through the channel 252. The assay material 1202 can both bind to the material of interest 504 on the removed capture objects 602 and exhibit a distinct, detectable behavior. For example, the assay material 1202 can contain a label that includes a binding substance that specifically binds the biological material of interest 504 (e.g., at a location on the material of interest 504 that is different than the location bound by the capture object 602). In the case where the biological material of interest 504 is an antibody, the label can include an Fc receptor and the capture object 602 can include an antigen bound by the antibody, or vice versa. In the example shown in FIGS. 12-14, the assay material 1202 can comprise labels that bind to the material of interest 504 on the capture objects and radiate energy 1402, as shown in FIG. 14. Thus, for example, the assay material 1202 can include a binding substance that specifically binds the biological material of interest 504 and is linked to a chromophore. In other embodiments, the assay material 1202 can include, e.g., a luciferase-linked binding substance that specifically binds the biological material of interest 504. In the latter case, the assay material 1202 can additionally include an appropriate luciferase substrate (e.g., a luciferin substrate). Thus, the assay material 1202 can fluoresce or luminescence. Regardless, the assay material 1202 can be provided to the removed capture objects 602 in sufficient quantity and for a sufficient time for assay material 1202 to bind to substantially all of the material of interest 504 bound to the removed capture objects 602.

As shown in FIG. 13, thereafter, assay material 1202 that has not bound to one of the removed capture objects 602 can be flushed out of the channel 252. For example, the flow 506 of assay material 1202 can be followed by a flow of medium 244 (or any washing material) in the channel 252, which can wash out of the channel 252 substantially all of the assay material 1202 that did not bind to material of interest 504 on the removed capture objects 602. As shown in FIG. 13, the capture objects 602 in the channel 252 can now comprise the material of interest 504 bound to the capture objects 602 and assay material 1202 bound to the material of interest 504.

As shown in FIG. 14, the assay material 1202 can radiate energy 1402, which can be detected by the detector 224. In some embodiments, the assay material 1202 may need to be stimulated (e.g., with light or other radiation, or a chemical catalyst or substrate (which can be flowed through the channel 252)) to trigger radiation of energy 1402. A detectable characteristic such as the level, brightness, color (e.g., specific wavelength), or the like of energy 1402 radiated from a removed capture object 602 can correspond to the amount of assay material 1202 bound to the removed capture object 602, which can correspond to the amount of biological material bound to the removed capture object 602, which in turn can correspond to the capability of the cell colony 500 in the pen 256 from which the capture object 602 was removed to produce the material of interest 504. In some embodiments, the assay material may be stimulated repeatedly. For example, light stimulus can be periodically administered, with any resulting radiation being detected following each stimulus. Alternatively, a chemical catalyst or substrate (e.g, luciferin) can be flowed into channel 252, whereupon detectable radiation can be detected. The channel 252 can be cleared of chemical catalyst after an appropriate period of time, after which the process can be repeated.

Step 412 can comprise detecting the level of energy 1402 radiating from each individual capture object 602 removed at step 408 from a pen 256. For example, the detector 224 can detect the level of energy 1402 from each removed capture object 602 in the channel 252. As noted with respect to step 410, the correlation between each removed capture object 602 and the pen 256 from which the capture object 602 was taken can be maintained, for example, in a digital table like Table 1 above. The level of energy 1402 radiated from each removed capture object 602 detected as part of step 412 can be stored in such a table, which as shown in Table 2 below, can include a column for the detected energy level.

TABLE 2

| Capture Object Location | Pen   | Energy Level |
|-------------------------|-------|--------------|
| Stop A                  | Pen 3 | Level ZZ     |
| Stop B                  | Pen 1 | Level XX     |
| Stop C                  | Pen 2 | Level YY     |

At step 414 of FIG. 4, the process 400 can identify holding pens 256 with desired cell colonies 500, and at least by default, also identify holding pens 256 with undesired cell colonies 500. For example, at step 414, the process 400 can determine which removed capture objects 602 radiated energy above (or below) a threshold level, and the correlated holding pens 256 of those removed capture objects 602 can be identified as having desired cell colonies 500. Holding pens 256 that correlate to removed capture objects 602 radiating 1402 at less than the threshold level can be identified as containing undesired cell colonies 500.

Rather than merely identifying holding pens 256 with desired and undesired cell colonies 500 at step 414, the process 400, in other embodiments, can quantitatively rate the cell colonies 500 in each holding pen 256 that corresponds to a removed capture object 602. For example, the process 400 can detect and quantify the energy 1402 radiated by each removed capture object 602, and thereby rate the capability of the cell colonies 500 in each of the holding pens 256 from which the removed capture objects 602 were taken to produce the material of interest 504.

In some embodiments, the detector 224 can capture images from which a human operator or the controller 230 can count or approximate the number of cells 502 in each of the holding pens 256 from which one of the removed capture objects 602 was taken. In such embodiments, the process 400 can utilize the radiated energy 1402 level (or other characteristic such as the color, brightness, or the like) detected as part of step 412 and the number of cells in a holding pen 256 to determine the capability of a colony 500 of cells 502 in a particular holding pen 256 to produce the material of interest 504 as a per cell 502 ratio. The process 400 can then utilize the foregoing to identify the holding pens 256 with desired cell colonies 500 at step 414.

Regardless, after step 414, the desired cell colonies 500 can be removed from their respective holding pens 256 to other locations in the device 200 or to other devices (not shown) for further processing, analysis, testing, or use. For example, the desired cell colonies 500 can be selected and moved as shown in U.S. patent application Ser. No. 14/520,150, filed Oct. 22, 2014, which is assigned to the same assignee as the instant application.

FIG. 4 is an example, and many variations of the process 400 are contemplated. For example, the process 400 can assess the biological activity at step 412 while the capture objects 602 are in the holding pens 256. The process 400, in some variations, thus need not include steps 408, 410 or steps 408, 410 can be skipped. As another example, all of the steps 402-414 need not be performed in the order shown in FIG. 4.

Figure 15:
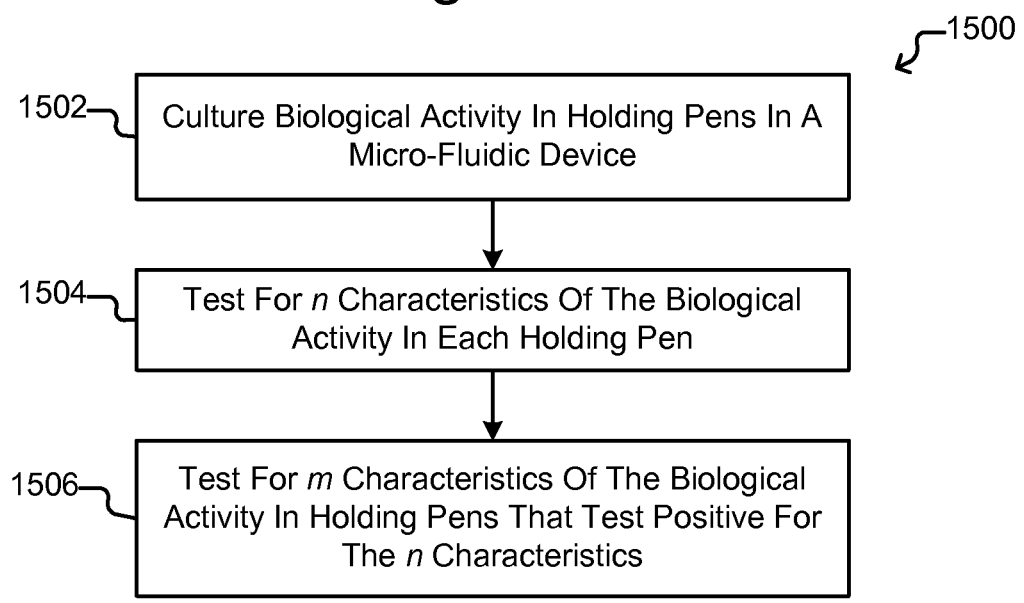
FIG. 15 illustrates an example of a process for testing biological activity in holding pens in a micro-fluidic device for a first number n of characteristics and then a second number m of characteristics according to some embodiments of the invention.

FIG. 15 illustrates yet another example of a process 1500 for assaying biological activity in holding pens of a micro-fluidic device. The process 1500 can be a narrower example of the more general process 100 in which, in the process 1500 of FIG. 15, the biological activity is tested for a first number n of characteristics and then tested for a second number m of characteristics, where n and m (which can be the same number or different numbers) can each be any whole number value one or greater. For ease of illustration and discussion, process 1500 is discussed below with respect to the micro-fluidic device 200 of FIGS. 2A-2C in which the selector 222 can be configured as illustrated in FIGS. 3A and 3B. The process 1500 is not so limited, however, and can thus be performed on other micro-fluidic devices.

As shown in FIG. 15, at step 1502, the process 1502 can culture biological activity in holding pens in a micro-fluidic device. Step 1502 can be performed like step 104 of FIG. 1 or step 402 in FIG. 4. For example, generally in accordance with the discussion above of FIG. 4, the biological activity can be the production of one or more different materials of interest by one or more biological cells in each pen 256 of the micro-fluidic device 200 of FIGS. 2A-2C. The culturing of step 1502 can be continuously preformed throughout execution of the process 1500, and the culturing of step 1502 can thus be continued during step 1504 and/or 1506.

At step 1504, the process 1500 can test the biological activity in each holding pen 256 for n characteristics each of which can be a different characteristic. The n characteristics can be any of the characteristics tested for in the process 100 or the process 400 of FIGS. 1 and 4 as discussed above or other characteristics of biological activity. Assessing multiple characteristics in this manner is desirable for numerous applications, including antibody characterization. Thus, for example, the multiple assessments can help with any of the following: identifying conformation specific antibodies (e.g., the different characteristics can be the ability of an antibody analyte to bind different conformations of a particular antigen); the epitope mapping of an antibody analyte (e.g., the different characteristics can be the ability to bind to various genetically or chemically altered forms of an antigen); assessing species cross-reactivity of an antibody analyte (e.g., the different characteristics can be the ability of antibody analyte to bind to homologous antigens originating from different species, such as human, mouse, rat, and/or other animals (e.g., experimental animals); and IgG isotyping of an antibody analyte (e.g., the different characteristics can be the ability to bind to IgG1, IgG2, IgG3, IgG4, IgM, IgA, IgE, and/or IgD). The generation of chemically modified antigen for epitope mapping of antibodies has been described, for example, in Dhungana et al. (2009), Methods Mol. Biol. 524:119-34. Other applications that can benefit from assessing multiple characteristics include, for example, detecting markers that correlate with cellular health, cancer, infection (e.g., viral, bacterial, parasitic, etc.), inflammation, response to therapeutic agents, and the like.

At step 1504, the process 1500 can perform tests that indicate whether the biological activity in each pen 256 has any one or more of the n characteristics. Thus, in some embodiments, the biological activity in a pen 256 is deemed to test positive at step 1504 if the biological activity has only one of the n characteristics. In other embodiments, the biological activity in a pen 256 is deemed to test positive at step 1504 only if the biological activity has all of the n characteristics, and in still other embodiments, the biological activity in a pen 256 is deemed to test positive at step 1504 if the biological activity has q number of the n characteristics, wherein q is greater than 1 but less than n.

At step 1506, the process 1500 can test the biological activity in each holding pen 256 that tested positive at step 1504 form different characteristics each of which can be a different characteristic. The m characteristics tested at step 1506 can be different than the n characteristics tested at step 1504. The m characteristics can include any of the characteristics tested for in the process 100 or the process 400 of FIGS. 1 and 4 as discussed above or other characteristics of a biological activity. Alternatively, there can be overlap between the m characteristics tested at step 1506 and the n characteristics tested at step 1504.

Step 1506 can be performed in any of the ways discussed above for performing step 1504. For example, at step 1506, the process 1500 can perform tests that indicate whether the biological activity in pens 256 that tested positive at step 1504 has any one or more of the m characteristics. Thus, in some embodiments, the biological activity in a pen 256 is deemed to test positive at step 1506 if the biological activity has only one of the m characteristics. In other embodiments, the biological activity in a pen 256 is deemed to test positive at step 1506 only if the biological activity has all of the m characteristics, and in still other embodiments, the biological activity in a pen 256 is deemed to test positive at step 1506 if the biological activity has p number of the m characteristics, wherein p is greater than 1 but less than m.

Figure 16:
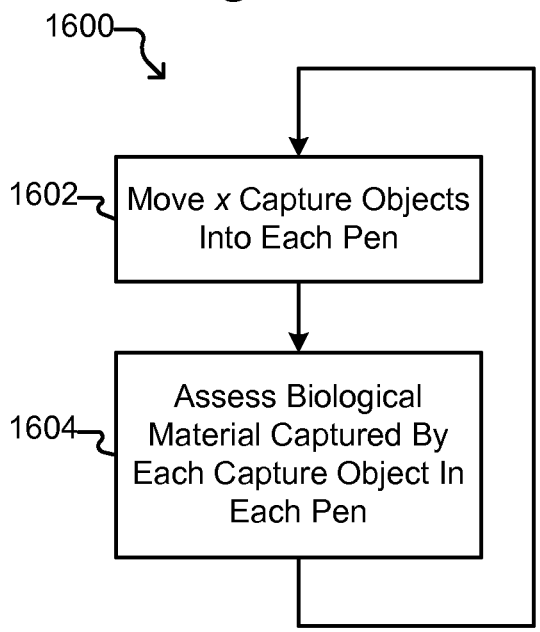
FIG. 16 is an example of a process for testing for the n characteristics and/or the m characteristics in the process of FIG. 15 according to some embodiments of the invention.
Figure 17:
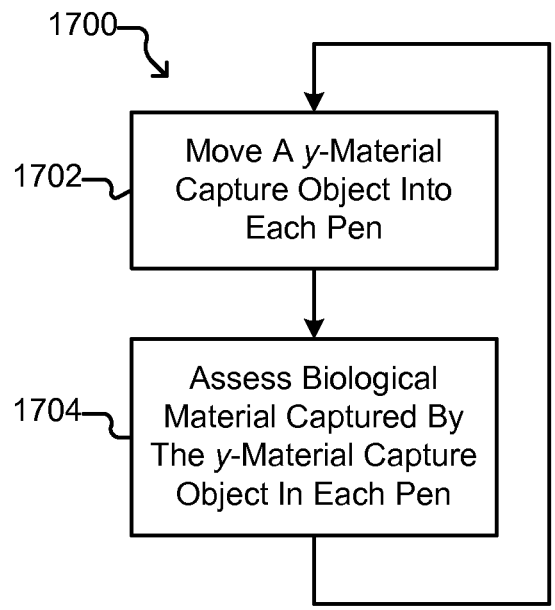
FIG. 17 is another example of a process for testing for the n characteristics and/or the m characteristics in the process of FIG. 15 according to some embodiments of the invention.

FIGS. 16 and 17 illustrate examples of process 1600, 1700 that can perform step 1504 and/or step 1506 of FIG. 15.

Figure 18:
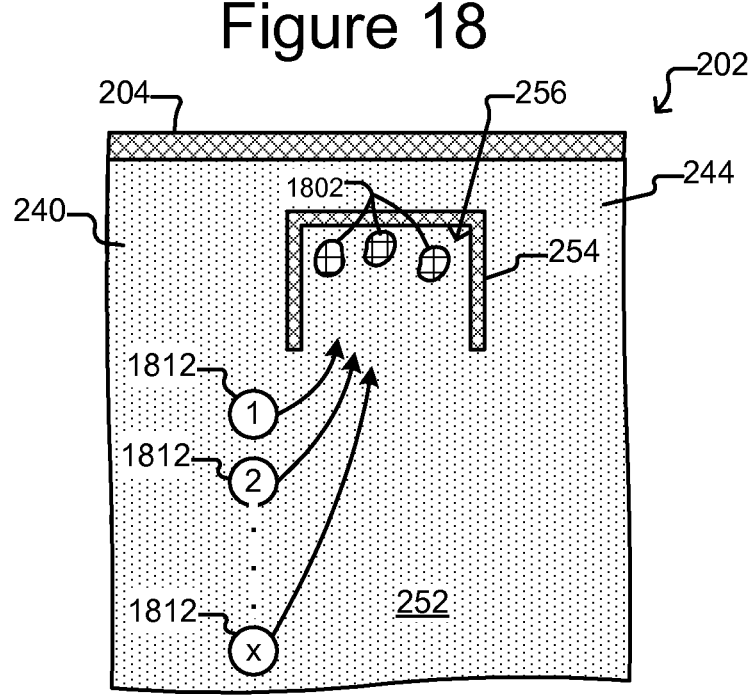
FIG. 18 illustrates an example of moving into a holding pen serially or in parallel a number x of capture objects each configured to bind a different material of interest according to some embodiments of the invention.

Turning first to FIG. 16, at step 1602, the process 1602 can move a number x of capture objects into each pen 256 of the micro-fluidic device 200. For example, the number x can be between 1 and n inclusive. FIG. 18 (which shows a top, cross-sectional view of a portion of the flow region 240 of the micro-fluidic device 200 of FIGS. 2A-2C) illustrates an example. As shown x capture objects 1812 can be moved into a pen 256. The capture objects 1812 can be moved into the pen 256 serially, in parallel, or in a combination of serially and parallel. Also shown, biological micro-objects 1802 can be in the pen 256. Although three biological micro-objects 1802 are shown in the pen 256, there can be one, two, or more than three. The biological micro-objects 1802 can be, for example, biological cells that produce one or more materials of interest.

Each capture object 1812 can comprise a binding substance that specifically binds to a particular biological material of interest. For example, the binding substance can have an affinity (e.g., Kd) for a particular biological material of interest of at least about 1 mM or stronger (e.g., about 100 µM, 10 µM, 1 µM, 500 nM, 400 nM, 300 nM, 200 nM 100 nM, 75 nM, 50 nM, 25 nM, 15 nM, 10 nM, 5 nM, 2.5 nM, 1 nM, or stronger). Such affinity can be, for example, two, three, four, five, ten, or more times stronger than the affinity for any material other than the particular biological material of interest (or at least any other biological material of interest present in the holding pen and/or the microfluidic device). Thus, for example, each capture object 1812 can comprise a different binding substance having such a predominate affinity for a different material of interest that may be present or produced by the biological activity being cultured in the pens 256 by step 1502 of FIG. 15. Otherwise, the capture objects 1812 can be generally similar to the capture objects 602, and the capture objects 1812 can be selected and moved in any of the ways discussed above for selecting and moving a capture object 602.

At step 1604, the process can assess biological material captured by each of the x capture objects moved into the pens 256 at step 1602. Step 1604 can be like, and can be performed in any manner discussed above with respect to, step 110 of FIG. 1 or step 414 of FIG. 4.

As illustrated in FIG. 16, the process 1600 can optionally be repeated any number of times. The number x can be the same or different for each repeated performance of step 1602. Thus, for example, the process 1600 can be performed one or more times until n capture objects (each of which can have a different binding substance) have been moved into a pen at step 1602 and assessed at step 1604. Thus, performing the process 1600 one or more times can result in moving a total of n capture objects into each pen by performing step 1602 one or more times, and assessing biological material captured by the n capture objects by performing step 1604 one or more times. For example, at each repeated performance of step 1602, the value of x can be any number between 1 and n−1, and the process 1600 can be repeated until the values of x at each repeated performance of step 1602 sum to at least n.

As noted, step 1504 and/or step 1506 of FIG. 15 can be performed by the process 1600 of FIG. 16. If step 1506 is performed, the number m is substituted for n in the above discussion of FIG. 16.

Figure 19:
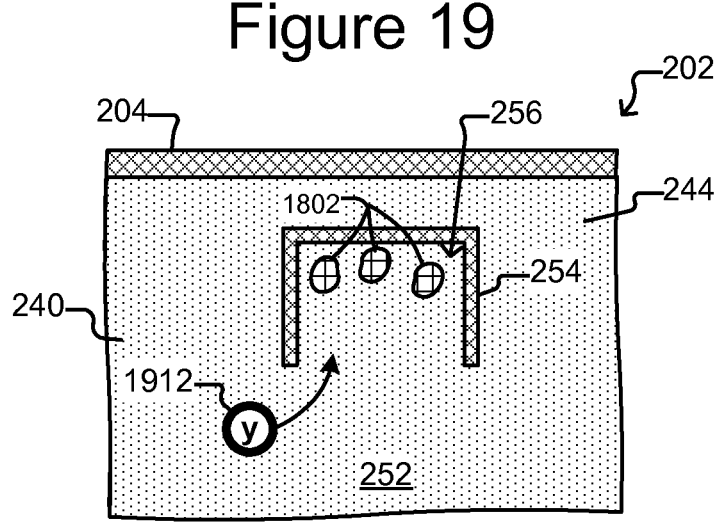
FIG. 19 shows an example of moving into a holding pen a capture object configured to bind a plurality of y different materials of interest according to some embodiments of the invention.

With reference now to FIG. 17, at step 1702, the process 1700 can move y-material capture objects into pens 256 of the micro-fluidic device 200, where each y-material capture object can comprise y different binding substances. The number y can be between 2 and n inclusive. FIG. 19 (which shows a top, cross-sectional view of a portion of the flow region 240 of the micro-fluidic device 200 of FIGS. 2A-2C) illustrates an example. As shown a y-material capture object 1912 can be moved into a pen 256 with one or more biological micro-objects 1802, which can be as discussed above.

The y-material capture object 1912 can comprise y different binding substances each of which specifically binds to a particular biological material of interest. For example, each binding substance can have an affinity (e.g., Kd) for a particular biological material of interest of at least about 1 mM or stronger (e.g., about 100 µM, 10 µM, 1 µM, 500 nM, 400 nM, 300 nM, 200 nM 100 nM, 75 nM, 50 nM, 25 nM, 15 nM, 10 nM, 5 nM, 2.5 nM, 1 nM, or stronger). Such affinity can be, for example, two, three, four, five, ten, or more times stronger than the affinity for any material other than the particular biological material of interest (or at least any other biological material of interest present in the holding pen and/or the microfluidic device). Otherwise, the y-material capture object 1912 can be generally similar to the capture objects 602, and the capture objects 1912 can be selected and moved in any of the ways discussed above for selecting and moving a capture object 602.

At step 1704, the process 1700 can assess biological material captured by the y-material capture object 1912 in each pen 256. Step 1704 can be like, and can be performed in any manner discussed above with respect to, step 110 of FIG. 1 or step 414 of FIG. 4.

As illustrated in FIG. 17, the process 1700 can optionally be repeated any number of times. The number y can the same or different for each repeated performance of step 1702. Thus, for example, the process 1700 can be performed one or more times until the values of y at each performance of step 1702 add to at least n. For example, at each repeated performance of step 1702, a value of y can be any number between 2 and n−2, and the process 1700 can be repeated until the values of y at each repeated performance of step 1702 sum to at least n.

As noted, step 1504 and/or step 1506 of FIG. 15 can be performed by the process 1700 of FIG. 17. If step 1506 is performed, the number m is substituted for n in the above discussion of FIG. 17.

Figure 20A:
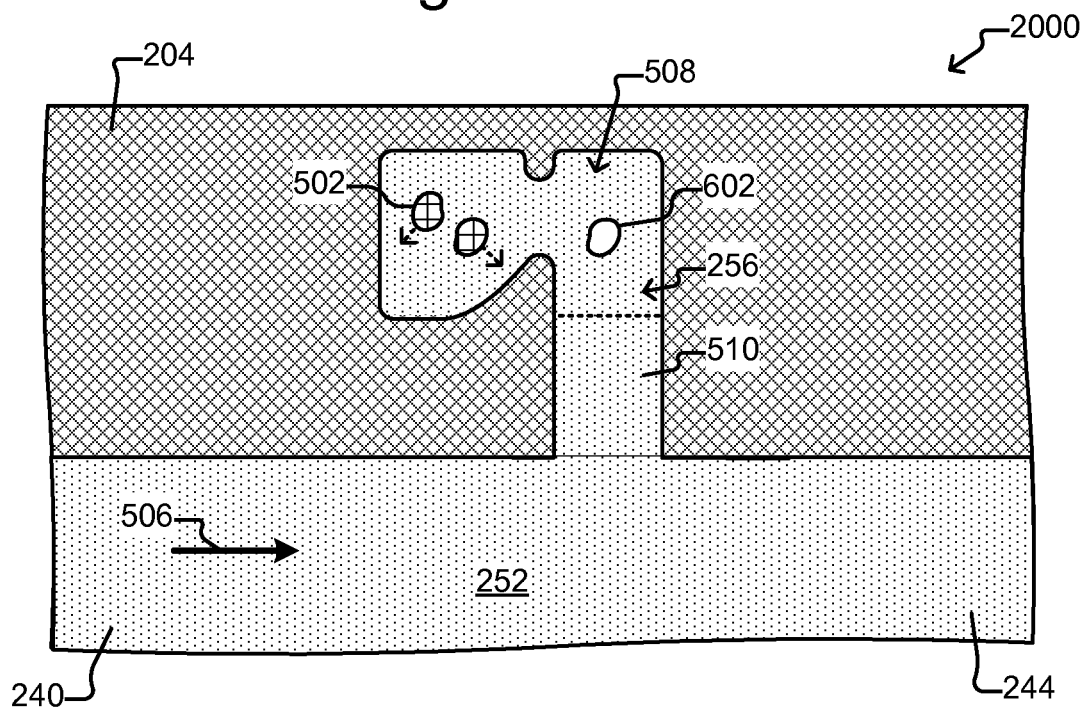
FIGS. 20A-20C illustrate examples of a holding pen that has a region for culturing biological cells and a separate region for placing capture micro-objects.
Figure 20B:
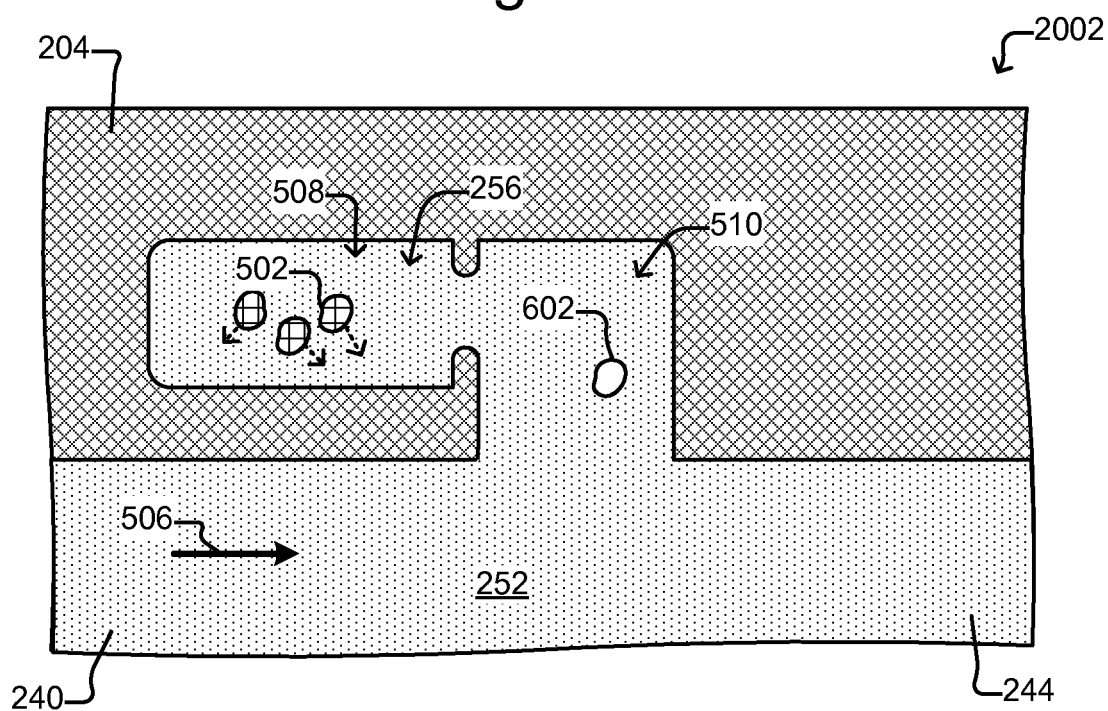
Figure 20C:
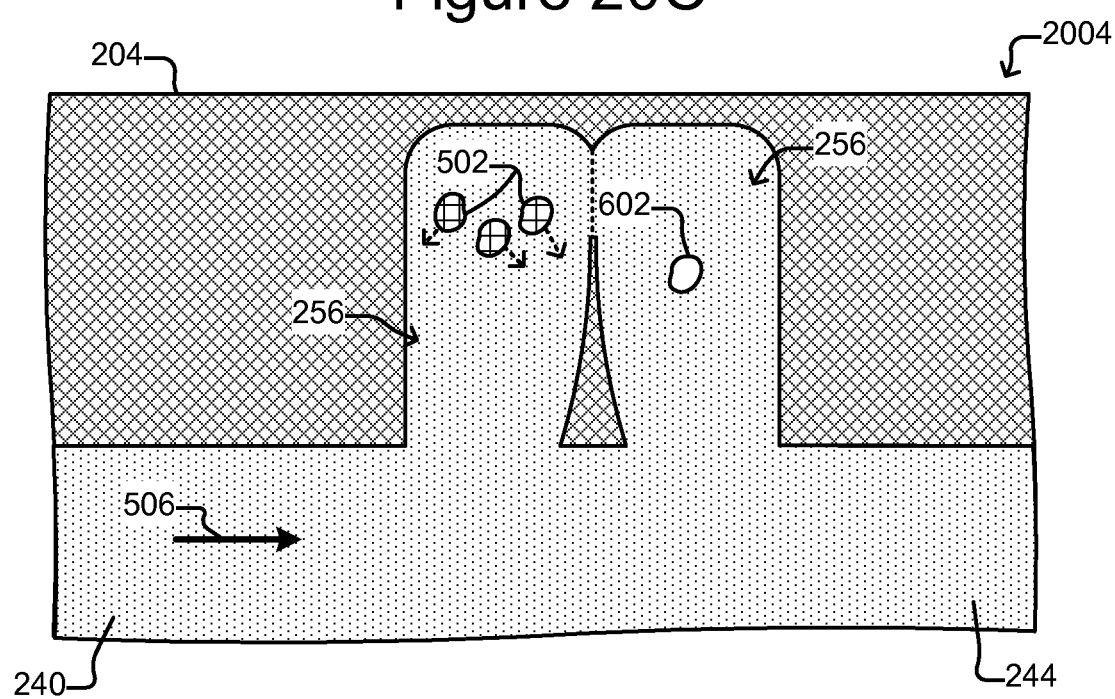

FIGS. 20A-20C show variations on the shape of holding pens which can be used in the micro-fluidic devices and methods of the invention. In each case, the holding pen includes a region that can be used to contain biological activity (e.g., one or more biological cells) and another region that can be used to contain capture objects 602. For example, in FIG. 20A, the holding pen 256 has an isolation region 508 that includes a left portion that can contain biological cells 502 and a right portion that can contain capture objects 602. The holding pen 256 further includes a connection region 510 having an proximal opening to channel 252 and a distal opening to the isolation region 508. In FIG. 20B, there is a similar arrangement, but holding pen 256 is longer and more shallow (in terms of the depth of the connection region 510). In FIG. 20C, the holding pen 256 includes a thin wall that separates a left portion which can contain biological cells 502 from a right portion which can contain capture objects 602. The thin wall is leaky and therefore allows diffusion of biological material of interest between the left and right portions of the holding pen 256, thereby preventing the biological activity (e.g., biological cells 502) from contacting the capture objects 602.

Although specific embodiments and applications of the invention have been described in this specification, these embodiments and applications are exemplary only, and many variations are possible.

What is claimed:

1. A micro-fluidic device comprising a housing wherein said housing comprises:
   a base;
   a micro-fluidic structure disposed on said base, wherein said micro-fluidic structure and said base define a flow region comprising a channel,
   a holding pen disposed on said base and disposed within said flow region, and
   an assay region comprising an assay chamber having an opening to said channel, wherein said assay chamber is located beside said holding pen,
   wherein said holding pen comprises an isolation region with a single opening, and a connection region, said connection region having a proximal opening to said channel and a distal opening to said isolation region; and
   wherein said assay region is located adjacent to said holding pen.

2. The micro-fluidic device of claim 1, wherein said assay chamber substantially lacks an isolation region.

3. The micro-fluidic device claim 1, wherein said device further comprises a means for generating a magnetic force within said microfluidic device.

4. The microfluidic device of claim 1, wherein said housing further comprises:
   a first electrode;
   a second electrode; and
   an electrode activation substrate,
   wherein said first electrode is part of a first wall of said housing and said second electrode and said electrode activation substrate are part of a second wall of said housing,
   wherein said electrode activation substrate has a surface comprising a plurality of DEP electrode regions, and
   wherein said surface of said electrode activation substrate is an inner surface of said flow region.

5. The microfluidic device of claim 4, wherein said electrode activation substrate is a photoconductive material.

6. The microfluidic device of claim 4, wherein said electrode activation substrate comprises a semiconductor material.

7. The microfluidic device of claim 6, wherein said semiconductor material comprises a plurality of doped layers, electrically insulating layers, and electrically conductive layers that form semiconductor integrated circuits.

8. A process of assaying biological activity in the micro-fluidic device of claim 1, said process comprising:
   culturing one or more biological cells in a holding pen of a micro-fluidic device, wherein said one or more cells produce n different biological materials of interest;
   introducing n different types of capture micro-objects into said holding pen, each said type of capture micro-object comprising a binding substance that specifically binds to one of said n different biological materials of interest;
   allowing said n different biological materials of interest produced by said one or more biological cells to bind to said n different types of capture micro-objects; and
   assessing binding between said n different biological materials of interest and said n different types of capture micro-objects.

9. The process of claim 8, wherein a result of said assessing is positive if at least one of said n different biological materials of interest specifically binds to one of said n different types of capture micro-objects.

10. The process of claim 8, wherein a result of said assessing is positive if at least two of said n different biological materials of interest each specifically binds to one of said n different types of capture micro-objects.

11. The process of claim 8, wherein a result of said assessing is positive if all n different biological materials of interest each specifically binds to one of said n different types of capture micro-objects.

12. The process of claim 8, wherein said n different types of capture micro-objects are introduced into said pen simultaneously.

13. The process of claim 8, wherein said n different types of capture micro-objects are introduced into said pen sequentially.

14. A micro-fluidic device comprising a housing wherein said housing comprises:
   a base;
   a micro-fluidic structure disposed on said base, wherein said micro-fluidic structure and said base define a flow region comprising a channel, a holding pen disposed on said base and disposed within said flow region, and an assay region comprising an assay chamber having an opening to said channel,
   wherein said holding pen comprises an isolation region with a single opening, and a connection region, said connection region having a proximal opening to said channel and a distal opening to said isolation region;
   wherein said assay region is located adjacent to said holding pen, and wherein said opening of said assay chamber is located directly across said channel from said proximal opening of said connection region of said holding pen.

15. The micro-fluidic device of claim 14, wherein said assay chamber substantially lacks an isolation region.

16. The micro-fluidic device claim 14, wherein said device further comprises a means for generating a magnetic force within said microfluidic device.

17. The microfluidic device of claim 14, wherein said housing further comprises:
   a first electrode;
   a second electrode; and
   an electrode activation substrate,
   wherein said first electrode is part of a first wall of said housing and said second electrode and said electrode activation substrate are part of a second wall of said housing, wherein said electrode activation substrate has a surface comprising a plurality of DEP electrode regions, and wherein said surface of said electrode activation substrate is an inner surface of said flow region.

18. The microfluidic device of claim 17, wherein said electrode activation substrate is a photoconductive material.

19. The microfluidic device of claim 17, wherein said electrode activation substrate comprises a semiconductor material.

20. The microfluidic device of claim 19, wherein said semiconductor material comprises a plurality of doped layers, electrically insulating layers, and electrically conductive layers that form semiconductor integrated circuits.

* * * * *

UNITED STATES PATENT AND TRADEMARK OFFICE
CERTIFICATE OF CORRECTION

PATENT NO. : 11,305,283 B2
APPLICATION NO. : 16/509166
DATED : April 19, 2022
INVENTOR(S) : Kevin T. Chapman et al.

It is certified that error appears in the above-identified patent and that said Letters Patent is hereby corrected as shown below:

In the Specification

Column 10, Line 23, "bathers" should be --barriers--
Column 10, Line 26, "bathers" should be --barriers--
Column 14, Line 37, "Bilogical" should be --Biological--
Column 16, Line 49, "bather" should be --barrier--
Column 22, Line 62, "form" should be --from--
Column 23, Line 16, "hasp" should be --has p--
Column 25, Line 43, --micro-fluidic-- should be inserted between --said-- and --device--
Column 25, Line 45, "microfluidic" should be --micro-fluidic--
Column 25, Line 46, "microfluidic" should be --micro-fluidic--
Column 25, Line 59, "microfluidic" should be --micro-fluidic--
Column 25, Line 61, "microfluidic" should be --micro-fluidic--
Column 25, Line 64, "microfluidic" should be --micro-fluidic--
Column 26, Line 3, "a" should be --the--
Column 26, Line 4, "a" should be --the--
Column 26, Line 31, --holding-- should be inserted between --said-- and --pen--
Column 26, Line 34, --holding-- should be inserted between --said-- and --pen--
Column 26, Line 56, --micro-fluidic-- should be inserted after --said--
Column 26, Line 58, "microfluidic" should be --micro-fluidic--
Column 26, Line 59, "microfluidic" should be --micro-fluidic--
Column 27, Line 5, "microfluidic" should be --micro-fluidic--
Column 27, Line 7, "microfluidic" should be --micro-fluidic--
Column 27, Line 10, "microfluidic" should be --micro-fluidic--

Signed and Sealed this
Thirteenth Day of September, 2022

Katherine Kelly Vidal
*Director of the United States Patent and Trademark Office*